(12) United States Patent
Schaffer et al.

(10) Patent No.: US 8,663,624 B2
(45) Date of Patent: Mar. 4, 2014

(54) ADENO-ASSOCIATED VIRUS VIRIONS WITH VARIANT CAPSID AND METHODS OF USE THEREOF

(75) Inventors: David V. Schaffer, Danville, CA (US);
Ryan R. Klimczak, Berkeley, CA (US);
James T. Koerber, Oakland, CA (US);
John G. Flannery, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/253,760

(22) Filed: Oct. 5, 2011

(65) Prior Publication Data

US 2012/0164106 A1 Jun. 28, 2012

Related U.S. Application Data

(60) Provisional application No. 61/390,497, filed on Oct. 6, 2010.

(51) Int. Cl.
*A01N 63/00* (2006.01)
*A01N 65/00* (2009.01)

(52) U.S. Cl.
USPC .................................. 424/93.6; 424/93.1

(58) Field of Classification Search
None
See application file for complete search history.

(56) References Cited

U.S. PATENT DOCUMENTS

| 7,629,322 | B2 * | 12/2009 | Kleinschmidt et al. ..... 514/44 R |
| 2005/0053922 | A1 | 3/2005 | Schaffer et al. |
| 2006/0292117 | A1 * | 12/2006 | Loiler et al. .................. 424/93.2 |
| 2007/0196338 | A1 * | 8/2007 | Samulski et al. ............ 424/93.2 |
| 2008/0269149 | A1 * | 10/2008 | Bowles et al. .................. 514/44 |
| 2009/0202490 | A1 | 8/2009 | Schaffer et al. |
| 2010/0172871 | A1 | 7/2010 | Flannery et al. |
| 2012/0093772 | A1 * | 4/2012 | Horsager et al. ............ 424/93.2 |

OTHER PUBLICATIONS

Choi et al, AAV Hybrid Serotypes: Improved Vectors for Gene Delivery. Current Gene Therapy, 2005: 5(3):299-310.*
Buch, et al., "In Contrast to AAC-Mediated *Cntf* Expression, AAV-Mediated *Gdnf* Expression Enhances Gene Replacement Therapy in Rodent Models of Retinal Degeneration", Molecular Therapy, Nov. 2006, vol. 14, No. 5, pp. 700-709.
Gregory-Evans, et al., "Ex vivo Gene Therapy Using Intravitreal Injection of GDNF-secreting Mouse Embryonic Stem Cells in a Rat Model of Retinal Degeneration", Molecular Vision, May 2009, vol. 15, pp. 962-973.
Klimczak, et al. "A Novel Adeno-Associated Viral Variant for Efficient and Selective Intravitreal Transduction of Rat Muller Cells", Plos One, Oct. 2009, vol. 4., Issue 10, pp. 1-10.
McGee, et al., "Glial Cell Line Derived Neurotrophic Factor Delays Photoreceptor in a Transgenic Rat Model of Retinitis Pigmentosa", Molecular Therapy, Dec. 2001, vol. 4, No. 6, pp. 622-629.

* cited by examiner

*Primary Examiner* — Joseph Woitach
*Assistant Examiner* — Kimberly A Aron
(74) *Attorney, Agent, or Firm* — Paula A. Borden; Bozicevic, Field & Francis LLP.

(57) ABSTRACT

The present disclosure provides adeno-associated virus (AAV) virions with altered capsid protein, where the AAV virions exhibit greater infectivity of retinal cells compared to wild-type AAV. The present disclosure further provides methods of delivering a gene product to a retinal cell in an individual, and methods of treating ocular disease.

36 Claims, 15 Drawing Sheets

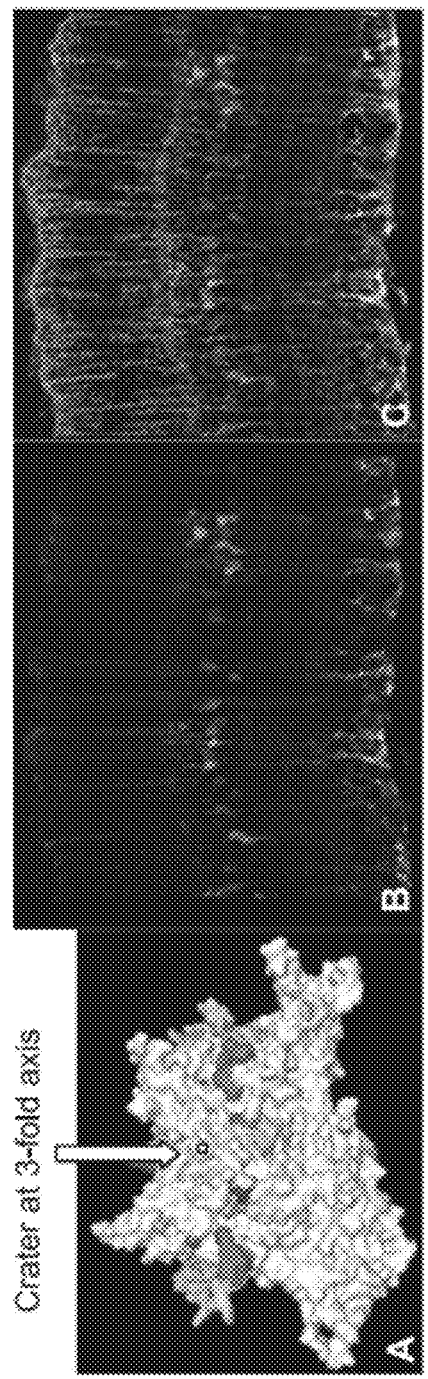

```
CAP6   MAADGYLPDWLEDNLSEGIREWWDLKPGAPKPKANQQKQDDGRGLVLPGYKYLGPFNGLDKGEPVNAADA
CAP2   MAADGYLPDWLEDTLSEGIRQWWDLKPGAPKPKANQQKQDDGRGLVLPGYKYLGPFNGLDKGEPVNAADA
ShH10  MAADGYLPDWLEDNLSEGIREWWALKPGAPQPKANQQHQDDNRGLVLPGYKYLGPFNGLDKGEPVNEADA
ShH13  MAADGYLPDWLEDTLSEGIRQWWKLKPGPPPPKPAERHKDDSRGLVLPGYKYLGPFNGLDKGEPVNAADA

CAP6   AALEHDKAYDQQLKAGDNPYLRYNHADAEFQERLQEDTSFGGNLGRAVFQAKKRVLEPFGLVEEGAKTAP
CAP2   AALEHDKAYDRQLDSGDNPYLRYNHADAEFQERLQEDTSFGGNLGRAVFQAKKRVLEPFGLVEEGAKTAP
ShH10  AALEHDKAYDQQLQAGDNPYLRYNHADAEFQERLQEDTSFGGNLGRAVFQAKKRVLEPLGLVEEGAKTAP
ShH13  AALEHDKAYDQQLKAGDNPYLKYNHADAEFQERLQEDTSFGGNLGRAVFQAKKRVLEPLGLVEEGAKTAP

CAP6   GKKRPVEQSPQ--EPDSSSGIGKTGQQPAKKRLNFGQTGDSESVPDPQPLGEPPATPAAVGPTTMASGGA
CAP2   GKKRPVEQSPQ--EPDSSSGIGKTGQQPAKKRLNFGQTGDSESVPDPQPLGEPPATPAAVGPTTMASGGA
ShH10  GKKRPVEPSPQ--RSPDSSTGIGKKGQQPARKRLNFGQTGDSESVPDPQPLGEPPATPAAVGPTTMASGGA
ShH13  GKKRPVEPSPQRSGDSSSGIGKTGQQPAKKRLNFGQTGDSESVPDPQPIGEPPAAPSGVGSNTMASGGA

CAP6   PMADNNEGADGVGNASGNWHCDSTWLGDRVITTSTRTWALPTYNNHLYKQIS-SASTGASNDNHYFGYST
CAP2   PMADNNEGADGVGNSSGNWHCDSTWLGDRVITTSTRTWALPTYNNHLYKQIS-SASTGASNDNHYFGYST
ShH10  PMADNNEGADGVGNASGNWHCDSTWLGDRVITTSTRTWALPTYNNHLYKQIS--QASNDNHYFGYST
ShH13  PMADNNEGADGVGNASGNWHCDSTWLGDRVITTSTRTWALPTYNNHLYKQIS-SASTGASNDNHYFGYST
```

FIG. 8A

```
CAP6   PWGYFDFNRFHCHFSPRDWQRLINNWGFRPKRLNPKLFNIQVKEVTTNDGVTTIANNLISTVQVFSDSE
CAP2   PWGYFDFNRFHCHFSPRDWQRLINNWGFRPKRLNPKLFNIQVKEVTTNDGVTTIANNLISTVQVFSDSE
Shh10  PWGYFDFNRFHCHFSPRDWQRLINNWGFRPKRLNFKLFNIQVKEVTNDGVTTIANNLISTVQVFSDSE
Shh13  PWGYFDFNRFHCHFSPRDWQRLINNWGFRPKRLNPKLFNIQVKEVTTNDGVTTIANNLISTVQVFSDSE

CAP6   YQLPYVLGSAHQGCLPFFADVFMIPQYGYLTLNMGSQAVGRSSFYCLEYFPSQMLRTGNNFTSYTFED
CAP2   YQLPYVLGSAHQGCLPFFADVFMIPQYGYLTLNMGSQAVGRSSFYCLEYFPSQMLRTGNNFTSYTFED
Shh10  YQLPYVLGSAHQGCLPFFADVFMIPQYGYLTLNNGSQAVGRSSFYCLEYFPSQMLRTGNNFTSYTFED
Shh13  YQLPYVLGSAHQGCLPFFADVFMIPQYGYLTLNNGSQAVGRSSFYCLEYFPSQMLRTGNNFTSYTFED

CAP6   VPFHSSYAHSQSLDRLMNPLIDQYLYYLNMTQNQSGSAQNKILLFSRGSPAGMSVQPKNWLFGPCYRQCR
CAP2   VPFHSSYAHSQSLDRLMNPLIDQYLYYLNMTQNQSGSAQNKILLFSRGSQAGASDIRLHSPNWLFGPCYRQCR
Shh10  VPFHSSYAHSQSLDRLMNPLIDQYLYLNRTQNQSGSAQNKDLLFSRGSPAGRSVQPRNWLFGPCYRQCR
Shh13  VPFHSSYAHSQSLDRLMNPLIDQYLYLNRTQNQSGSAQNKDLLFSRGSPAGMSVQPRNWLFGPCYRQCR

CAP6   VSKKTDNNNSNFTWTQASKYNLNGRESTINPGTAMASHKDDKDMFFPNSGVMIFGRESAGASNTALDNV
CAP2   VSKTEDNNNSEYSTCAYDKVQLNPMAHKDMASHKDDKDMFFPFFDEFRFGVVFCMAGGGSEKTIDIEYVGASNTALDNV
Shh10  VSKTKTDMNNSNFTWTCASKYNLNCRESTINPGTAMASHKDDFKDMFFPNSGVMIFGKESAGASNTALDNV
Shh13  VSKTKTDMNNSNFTWTQASKYNLNGRESTINPGTAMASHKDDKDMFFPNSGVMIFGKESAGASNTALDNV
```

FIG. 8B

SEQUENCE LISTING

<160> NUMBER OF SEQ ID NOS: 11

<210> SEQ ID NO 1
<211> LENGTH: 736
<212> TYPE: PRT

<213> ORGANISM: Adenoassociated virus

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe

```
                    405                 410                 415
Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 2
<211> LENGTH: 736
<212> TYPE: PRT
<213> ORGANISM: Adenoassociated virus

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
```

```
                50                  55                  60
Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Pro Val Lys Thr Ala Pro Gly Lys Lys Arg
130                 135                 140

Pro Val Glu His Ser Pro Val Glu Glu Pro Asp Ser Ser Ser Gly Thr
145                 150                 155                 160

Gly Lys Ala Gly Gln Gln Pro Ala Arg Lys Arg Leu Asn Phe Gly Gln
                165                 170                 175

Thr Gly Asp Ala Asp Ser Val Pro Asp Pro Gln Pro Leu Gly Gln Pro
                180                 185                 190

Pro Ala Ala Pro Ser Gly Leu Gly Thr Asn Thr Met Ala Thr Gly Ser
                195                 200                 205

Gly Ala Pro Met Ala Asp Asn Asn Glu Gly Ala Asp Gly Val Gly Asn
210                 215                 220

Ser Ser Gly Asn Trp His Cys Asp Ser Thr Trp Met Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
                260                 265                 270

Tyr Phe Gly Tyr Ser Thr Pro Trp Gly Tyr Phe Asp Phe Asn Arg Phe
                275                 280                 285

His Cys His Phe Ser Pro Arg Asp Trp Gln Arg Leu Ile Asn Asn Asn
                290                 295                 300

Trp Gly Phe Arg Pro Lys Arg Leu Asn Phe Lys Leu Phe Asn Ile Gln
305                 310                 315                 320

Val Lys Glu Val Thr Gln Asn Asp Gly Thr Thr Thr Ile Ala Asn Asn
                325                 330                 335

Leu Thr Ser Thr Val Gln Val Phe Thr Asp Ser Glu Tyr Gln Leu Pro
                340                 345                 350

Tyr Val Leu Gly Ser Ala His Gln Gly Cys Leu Pro Pro Phe Pro Ala
                355                 360                 365

Asp Val Phe Met Val Pro Gln Tyr Gly Tyr Leu Thr Leu Asn Asn Gly
                370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Ser Arg
                435                 440                 445

Thr Asn Thr Pro Ser Gly Thr Thr Thr Gln Ser Arg Leu Gln Phe Ser
                450                 455                 460

Gln Ala Gly Ala Ser Asp Ile Arg Asp Gln Ser Arg Asn Trp Leu Pro
465                 470                 475                 480
```

```
Gly Pro Cys Tyr Arg Gln Gln Arg Val Ser Lys Thr Ser Ala Asp Asn
                485                 490                 495

Asn Asn Ser Glu Tyr Ser Trp Thr Gly Ala Thr Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Gln Ser Gly Val Leu Ile Phe Gly
    530                 535                 540

Lys Gln Gly Ser Glu Lys Thr Asn Val Asp Ile Glu Lys Val Met Ile
545                 550                 555                 560

Thr Asp Glu Glu Glu Ile Arg Thr Thr Asn Pro Val Ala Thr Glu Gln
                565                 570                 575

Tyr Gly Ser Val Ser Thr Asn Leu Gln Arg Gly Asn Arg Gln Ala Ala
            580                 585                 590

Thr Ala Asp Val Asn Thr Gln Gly Val Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Ser Thr Thr Phe Ser Ala Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Variant Adenoassociated virus

<400> SEQUENCE: 3

Met Ala Ala Asp Gly Tyr Leu Pro Asp Trp Leu Glu Asp Asn Leu Ser
 1               5                  10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
 65                 70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Phe Gly Leu Val Glu Glu Gly Ala Lys Thr Ala Pro Gly Lys Lys Arg
            130                 135                 140
Pro Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
                180                 185                 190
Ala Thr Pro Ala Ala Val Gly Pro Thr Thr Met Ala Ser Gly Gly Gly
                195                 200                 205
Ala Pro Met Ala Asp Asn Asn Glu Gly Ala Asp Gly Val Gly Asn Ala
            210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
                260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
            290                 295                 300
Trp Gly Phe Arg Pro Lys Arg Leu Asn Phe Lys Leu Phe Asn Val Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
                340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
            370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Asp Val Pro Phe His Ser Ser Tyr Ala His Ser Gln Ser Leu Asp
                420                 425                 430
Arg Leu Met Asn Pro Leu Ile Asp Gln Tyr Leu Tyr Tyr Leu Asn Arg
            435                 440                 445
Thr Gln Asp Gln Ser Gly Ser Ala Gln Asn Lys Asp Leu Leu Phe Ser
            450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
            515                 520                 525
Asp Asp Lys Asn Lys Phe Phe Pro Met Ser Gly Val Met Ile Phe Gly
            530                 535                 540
Lys Glu Ser Ala Gly Ala Ser Asn Thr Ala Leu Asp Asn Val Met Ile
545                 550                 555                 560
```

```
Thr Asp Glu Glu Glu Ile Lys Ala Thr Asn Pro Val Ala Thr Glu Arg
                565                 570                 575

Phe Gly Thr Val Ala Val Asn Leu Gln Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 4
<211> LENGTH: 737
<212> TYPE: PRT
<213> ORGANISM: Variant Adenoassociated virus

<400> SEQUENCE: 4

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Thr Pro Ala Ala Val Gly Pro Thr Thr Met Ala Ser Gly Gly
        195                 200                 205
```

```
Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Asn
        435                 440                 445

Arg Thr Gln Asn Gln Ser Gly Ser Ala Gln Asn Lys Asp Leu Leu Phe
    450                 455                 460

Ser Arg Gly Ser Pro Ala Gly Met Ser Val Gln Pro Lys Asn Trp Leu
465                 470                 475                 480

Pro Gly Pro Cys Tyr Arg Gln Gln Arg Val Ser Lys Thr Lys Thr Asp
                485                 490                 495

Asn Asn Asn Ser Asn Phe Thr Trp Thr Gly Ala Ser Lys Tyr Asn Leu
            500                 505                 510

Asn Gly Arg Glu Ser Ile Ile Asn Pro Gly Thr Ala Met Ala Ser His
        515                 520                 525

Lys Asp Asp Lys Asp Lys Phe Phe Pro Met Ser Gly Val Met Ile Phe
    530                 535                 540

Gly Lys Glu Ser Ala Gly Ala Ser Asn Thr Ala Leu Asp Asn Val Met
545                 550                 555                 560

Ile Thr Asp Glu Glu Glu Ile Lys Ala Thr Asn Pro Val Ala Thr Glu
                565                 570                 575

Arg Phe Gly Thr Val Ala Val Asn Leu Gln Ser Ser Ser Thr Asp Pro
            580                 585                 590

Ala Thr Glu Asp Val His Val Met Gly Ala Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly His Phe His Pro Ser Pro Leu Met Gly Gly Phe Gly
```

```
                625                 630                 635                 640
Leu Lys Asn Pro Pro Gln Ile Leu Ile Lys Asn Thr Pro Val Pro
                    645                 650                 655

Ala Asn Pro Pro Ala Glu Phe Ser Ala Thr Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Val Gln Tyr Thr Ser
    690                 695                 700

Asn Tyr Ala Lys Ser Ala Asn Val Asp Phe Thr Val Asp Asn Gly
705                 710                 715                 720

Leu Tyr Thr Glu Pro Arg Pro Ile Gly Thr Arg Tyr Leu Thr Arg Asn
                    725                 730                 735

Leu

<210> SEQ ID NO 5
<211> LENGTH: 736
<212> TYPE: PRT
<213> ORGANISM: Variant Adenoassociated virus

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270
```

```
Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Val Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asp Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Lys Asn Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
```

```
                690                 695                 700
Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 6
<211> LENGTH: 736
<212> TYPE: PRT
<213> ORGANISM: Variant Adenoassociated virus

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Val Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
```

```
                    340                 345                 350
Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
                435                 440                 445

Thr Gln Asp Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
                515                 520                 525

Asp Asp Lys Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
                595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 7
<211> LENGTH: 736
<212> TYPE: PRT
<213> ORGANISM: Variant Adenoassociated virus
```

-continued

```
<400> SEQUENCE: 7

Met Ala Ala Asp Gly Tyr Leu Pro Asp Trp Leu Glu Asp Asn Leu Ser
 1               5                  10                  15

Glu Gly Ile Arg Glu Trp Trp Asp Leu Lys Pro Gly Ala Pro Lys Pro
             20                  25                  30

Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415
```

-continued

```
Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asp Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asn Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 8
<211> LENGTH: 736
<212> TYPE: PRT
<213> ORGANISM: Variant Adenoassociated virus

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
            35                  40                  45

Gly Tyr Lys Tyr Leu Gly Pro Phe Asn Gly Leu Asp Lys Gly Glu Pro
50                  55                  60
```

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Val Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495
```

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
        580                 585                 590

Thr Gly Asp Val His Val Met Gly Ala Leu Pro Gly Met Val Trp Gln
    595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
        660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
            705                 710                 715                 720

Tyr Thr Glu Pro Arg Pro Ile Gly Thr Arg Tyr Leu Thr Arg Pro Leu
            725                 730                 735

<210> SEQ ID NO 9
<211> LENGTH: 736
<212> TYPE: PRT
<213> ORGANISM: Variant Adenoassociated virus

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Phe Gly Leu Val Glu Glu Gly Ala Lys Thr Ala Pro Gly Lys Lys Arg
130                 135                 140

```
Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gln Thr
            165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
                195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Val Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asn Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
```

```
                    565                 570                 575
Phe Gly Thr Val Ala Val Asn Leu Gln Ser Ser Thr Asp Pro Ala
                580                 585                 590

Thr Gly Asp Val His Val Met Gly Ala Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
                    645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 10
<211> LENGTH: 211
<212> TYPE: PRT
<213> ORGANISM: Homo sapiens

<400> SEQUENCE: 10

Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
                20                  25                  30

Ala Glu Asp Arg Ser Leu Gly Arg Arg Arg Ala Pro Phe Ala Leu Ser
            35                  40                  45

Ser Asp Ser Asn Met Pro Glu Asp Tyr Pro Asp Gln Phe Asp Asp Val
50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Asp Leu Ser Phe Leu Asp
            180                 185                 190

Asp Asn Leu Val Tyr His Ile Leu Arg Lys His Ser Ala Lys Arg Cys
        195                 200                 205

Gly Cys Ile
```

-continued

<210> SEQ ID NO 11
<211> LENGTH: 418
<212> TYPE: PRT
<213> ORGANISM: Homo sapiens

<400> SEQUENCE: 11

Met Gln Ala Leu Val Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Asp Pro Phe Phe Lys
        35                  40                  45

Val Pro Val Asn Lys Leu Ala Ala Val Ser Asn Phe Gly Tyr Asp
50                  55                  60

Leu Tyr Arg Val Arg Ser Ser Thr Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
                115                 120                 125

Val Thr Ala Pro Gln Lys Asn Leu Lys Ser Ala Ser Arg Ile Val Phe
130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
                195                 200                 205

Gly Val Ala His Phe Lys Gly Gln Trp Val Thr Lys Phe Asp Ser Arg
210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
                260                 265                 270

Ser Ile Ile Phe Phe Leu Pro Leu Lys Val Thr Gln Asn Leu Thr Leu
                275                 280                 285

Ile Glu Glu Ser Leu Thr Ser Glu Phe Ile His Asp Ile Asp Arg Glu
290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
                340                 345                 350

Leu Thr Gln Val Glu His Arg Ala Gly Phe Glu Trp Asn Glu Asp Gly
                355                 360                 365

Ala Gly Thr Thr Pro Ser Pro Gly Leu Gln Pro Ala His Leu Thr Phe

-continued

```
            370                 375                 380
Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro
```

ADENO-ASSOCIATED VIRUS VIRIONS WITH VARIANT CAPSID AND METHODS OF USE THEREOF

STATEMENT REGARDING FEDERALLY SPONSORED RESEARCH

This invention was made with government support under Grant No. R21EY016994 awarded by the National Institutes of Health. The government has certain rights in the invention.

BACKGROUND

The pathologies of numerous retinal degenerative diseases can be attributed to a multitude of genetic factors, and individualized treatment options for afflicted patients are limited and cost-inefficient. Gene delivery of secretable neuroprotective factors to Müller cells, a type of retinal glia that contacts all classes of retinal neurons, represents an ideal approach to mediate protection of the entire retina. Vehicles such as adeno-associated viral vector (AAV) are currently in use for the delivery of gene products. Although several naturally occurring AAV variants have been isolated with a variety of tropisms, or cellular specificities, these vectors inefficiently infect Müller cells via intravitreal injection.

AAV belongs to the Parvoviridae family and Dependovirus genus, whose members require co-infection with a helper virus such as adenovirus to promote replication, and AAV establishes a latent infection in the absence of a helper. Virions are composed of a 25 nm icosahedral capsid encompassing a 4.9 kb single-stranded DNA genome with two open reading frames: rep and cap. The non-structural rep gene encodes four regulatory proteins essential for viral replication, whereas cap encodes three structural proteins (VP1-3) that assemble into a 60-mer capsid shell. This viral capsid mediates the ability of AAV vectors to overcome many of the biological barriers of viral transduction—including cell surface receptor binding, endocytosis, intracellular trafficking, and unpackaging in the nucleus.

LITERATURE

U.S. Patent Publication No. 2005/0053922; U.S. Patent Publication No. 2009/0202490; McGee et al. (2001) *Mol. Ther.* 4:622; Buch et al. (2006) *Mol. Ther.* 14:700; Gregory-Evans et al. (2009) *Mol. Vis.* 15:962; U.S. Patent Publication No. 2010/0172871; Klimczak, et al. (2009) *PLoS One* 4: e7467.

SUMMARY OF THE INVENTION

The present disclosure provides adeno-associated virus (AAV) virions with altered capsid protein, where the AAV virions exhibit greater infectivity of retinal cells compared to wild-type AAV. The present disclosure further provides methods of delivering a gene product to a retinal cell in an individual, and methods of treating ocular disease.

BRIEF DESCRIPTION OF THE DRAWINGS

FIGS. 7A-C depict rAAV6 N451D expression following intravitreal injection.

FIGS. 8A-C depict amino acid sequences of wild-type and variant AAV capsids.

DEFINITIONS

Figure 1:
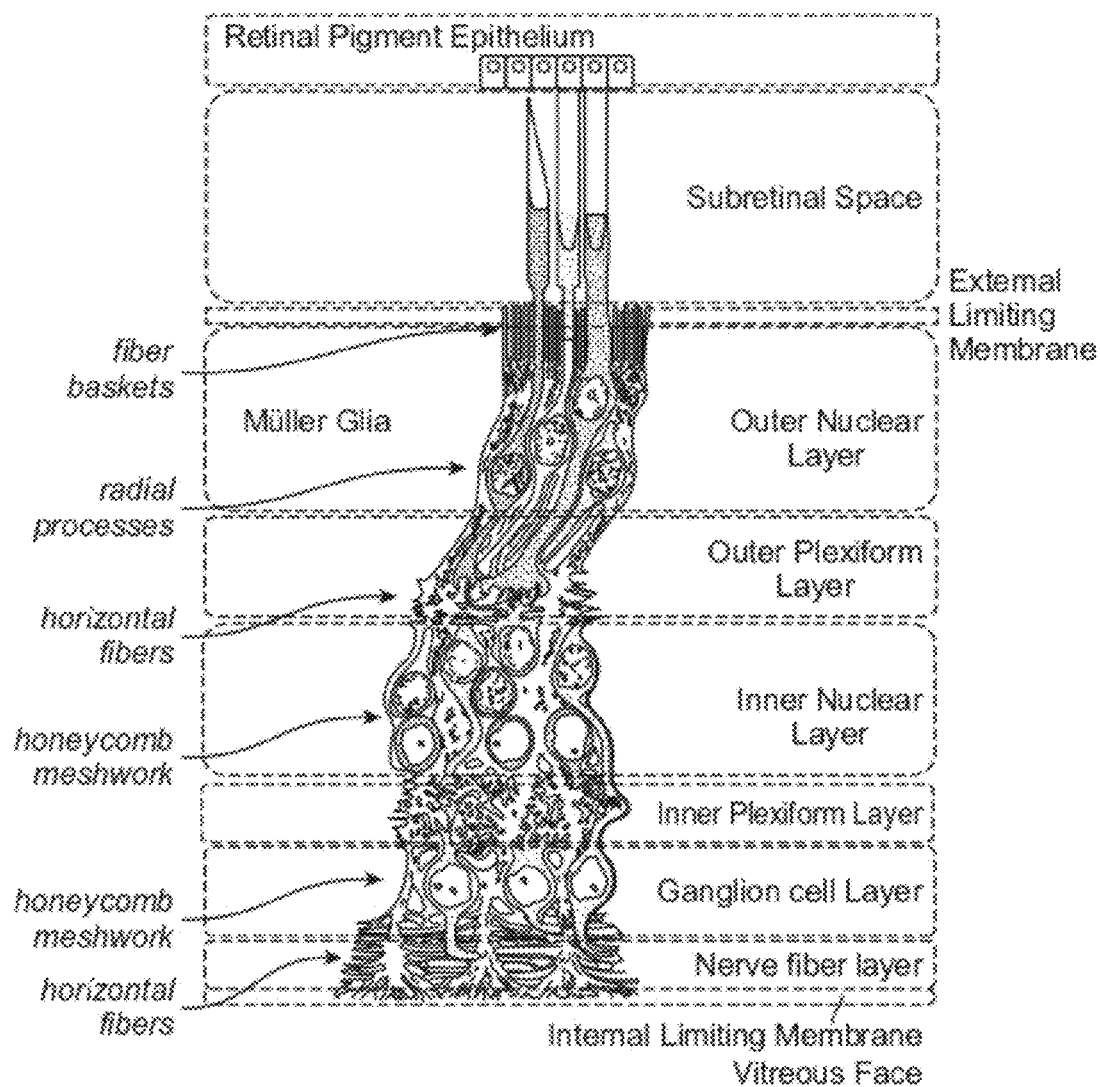
FIG. 1 depicts Müller glia in the retina.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome, such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Ban viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virus or viral particle is one that comprises a polynucleotide component which it is capable of delivering into a cell for which the viral species is tropic. The term does not necessarily imply any replication capacity of the virus. As used herein, an "infectious" virus or viral particle is one that can access a target cell, can infect a target cell, and can express a heterologous nucleic acid in a target cell. Thus, "infectivity" refers to the ability of a viral particle to access a target cell, infect a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA).

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970)

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;
Gap Penalty: 1.00;
Gap Size Penalty: 0.33; and
Joining Penalty: 30.0.

A "gene" refers to a polynucleotide containing at least one open reading frame that is capable of encoding a particular protein after being transcribed and translated.

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA that is a fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a recombinant AAV virion" includes a plurality of such virions and reference to "the Müller cell" includes reference to one or more Müller cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides adeno-associated virus (AAV) virions with altered capsid protein, where the AAV virions exhibit greater infectivity of retinal cells compared to wild-type AAV. The present disclosure further provides methods of delivering a gene product to a retinal cell in an individual, and methods of treating ocular disease.

Recombinant Adeno-Associated Virus Virions

The present disclosure provides an infectious, recombinant adeno-associated virus (rAAV) virion comprising: a) a variant AAV capsid protein, where the variant AAV capsid protein comprises at least one amino acid difference (e.g., amino acid substitution, amino acid insertion, amino acid deletion) relative to a corresponding parental AAV capsid protein, and where the variant capsid protein confers increased infectivity of a retinal cell (e.g., a Müller glial cell (also referred to herein as a "Müller cell")) compared to the infectivity of the retinal cell (e.g., Müller glial) cell by an AAV virion comprising the corresponding parental AAV capsid protein, where the AAV capsid protein does not comprise an amino acid sequence present in a naturally occurring AAV capsid protein; and b) a heterologous nucleic acid comprising a nucleotide sequence encoding a heterologous gene product. In some embodiments, the parental AAV capsid protein is a wild-type AAV capsid. For example, in some embodiments, the parental AAV capsid protein is wild-type AAV6 capsid protein. In some cases, the AAV capsid protein comprises an amino acid sequence having at least about 85%, at least about 90%, at least about 95%, at least about 98%, at least about 99%, or 100%, amino acid sequence identity to the ShH10 amino acid sequence depicted in FIGS. 8A-C, where the AAV capsid protein does not comprise an amino acid sequence present in a naturally occurring AAV capsid protein.

A subject rAAV virion exhibits at least 5-fold, at least 10-fold, at least 15-fold, at least 20-fold, at least 25-fold, at least 50-fold, or more than 50-fold, increased infectivity of a retinal cell compared to the infectivity of the retinal cell by an AAV virion comprising the corresponding parental AAV capsid protein (e.g., a wild-type AAV capsid protein). For example, subject rAAV virion exhibits at least 5-fold, at least 10-fold, at least 15-fold, at least 20-fold, at least 25-fold, at least 50-fold, or more than 50-fold, increased infectivity of a retinal cell compared to the infectivity of the retinal cell by an AAV virion comprising a wild-type AAV6 capsid protein.

For example, in some cases, a subject rAAV virion exhibits at least 5-fold, at least 10-fold, at least 15-fold, at least 20-fold, at least 25-fold, at least 50-fold, or more than 50-fold, increased infectivity of a Müller glial cell compared to the infectivity of the Müller glial cell by an AAV virion comprising the corresponding parental AAV capsid protein (e.g., a wild-type AAV capsid protein). For example, in some cases, a subject rAAV virion exhibits at least 5-fold, at least 10-fold, at least 15-fold, at least 20-fold, at least 25-fold, at least 50-fold, or more than 50-fold, increased infectivity of a Müller glial cell compared to the infectivity of the Müller glial cell by an AAV virion comprising a wild-type AAV6 capsid protein.

Without being bound to theory, increased infectivity of a retinal cell such as a Müller glial cell, when a subject rAAV virion is administered via intravitreal injection, may be due to altered interactions with naturally-occurring structures in the eye, e.g., increased ability of the rAAV virion to cross the inner limiting membrane.

In some embodiments, a subject rAAV virion selectively infects a Müller glial cell, e.g., a subject rAAV virion infects a Müller glial cell with 5-fold, 10-fold, 15-fold, 20-fold, 25-fold, 50-fold, or more than 50-fold, specificity than a non-Müller glial cell present in the eye, e.g., a retinal ganglion cell.

In some cases, a subject rAAV virion, when introduced (e.g., via intravitreal injection or other route of administration) into an eye of an individual, provides for high level production of the heterologous gene product encoded by the rAAV in the eye. For example, a heterologous polypeptide encoded by the rAAV can be produced in the eye at a level of from about 1 µg to about 50 µg, or greater than 50 µg. As another example, a heterologous polypeptide encoded by the rAAV can be produced in the vitreous fluid of the eye at a level of from about 100 pg/mL to about 5000 pg/mL vitreous fluid, e.g., from about 100 pg/mL to about 500 pg/mL, from about 500 pg/mL to about 1000 pg/mL, from about 1000 pg/mL to about 2000 pg/mL, from about 2000 pg/mL to about 3000 pg/mL, from about 3000 pg/mL to about 4000 pg/mL, or from about 4000 pg/mL to about 5000 pg/mL. In some cases, a polypeptide encoded by the rAAV can be produced in the vitreous fluid of the eye at a level of greater than 5000 pg/mL vitreous fluid.

In some cases, a subject rAAV virion, when introduced (e.g., via intravitreal injection or other route of administration) into an eye of an individual, provides for production of the heterologous gene product encoded by the rAAV in at least about 10%, at least about 15%, at least about 20%, at least about 25%, at least about 30%, at least about 35%, at least about 40%, at least about 50% at least about 60%, at least about 70%, at least about 80%, or more than 80%, of the Müller cells in the eye.

In some embodiments, a subject rAAV virion, when introduced (e.g., via intravitreal injection) into an eye of an individual, provides for production of the heterologous gene product encoded by the rAAV for a period of time of from about 2 days to about 6 months, e.g., from about 2 days to about 7 days, from about 1 week to about 4 weeks, from about 1 month to about 2 months, or from about 2 months to about 6 months. In some embodiments, a subject rAAV virion, when introduced (e.g., via intravitreal injection) into an eye of an individual, provides for production of the heterologous gene product encoded by the rAAV for a period of time of more than 6 months, e.g., from about 6 months to 20 years or more, or greater than 1 year, e.g., from about 6 months to about 1 year, from about 1 year to about 2 years, from about 2 years to about 5 years, from about 5 years to about 10 years, from about 10 years to about 15 years, from about 15 years to about 20 years, or more than 20 years.

Heterologous Nucleic Acid

A subject rAAV virion comprises a heterologous nucleic acid comprising a nucleotide sequence encoding a heterologous gene product, e.g., a nucleic acid gene product or a polypeptide gene product. In some embodiments, the gene product is an interfering RNA (e.g., shRNA, siRNA, miRNA). In some embodiments, the gene product is an aptamer. The gene product can be a self-complementary nucleic acid. In some embodiments, the gene product is a polypeptide.

Nucleic Acid Gene Products

Suitable nucleic acid gene products include interfering RNA, antisense RNA, ribozymes, and aptamers. Where the gene product is an interfering RNA (RNAi), suitable RNAi include RNAi that decrease the level of an angiogenic factor in a cell. For example, an RNAi can be a miRNA, an shRNA, or an siRNA that reduces the level of vascular endothelial growth factor (VEGF) in a cell.

Where the gene product is an interfering RNA (RNAi), suitable RNAi include RNAi that decrease the level of an angiogenic factor in a cell. For example, an RNAi can be an shRNA or siRNA that reduces the level of VEGF or VEGF receptor (VEGFR) in a cell. RNAi agents that target VEGF include, e.g., an RNAi described in U.S. Patent Publication No. 2011/0224282. For example, an siRNA specific for VEGF-A, VEGFR1, or VEGFR2 would be suitable. Suitable nucleic acid gene products also include a ribozyme specific for VEGF-A, VEGFR1, or VEGFR2; an antisense specific for VEGF-A, VEGFR1, or VEGFR2; siRNA specific for VEGF-A, VEGFR1, or VEGFR2; etc.

Also suitable as a gene product is an miRNA that reduces the level of VEGF by regulating VEGF gene expression, e.g., through post-transcriptional repression or mRNA degradation. Examples of suitable miRNA include, e.g., miR-15b, miR-16, miR-20a, and miR-20b. See, e.g., Hua et al. (2006) *PLoS ONE* 1:e116.

Also suitable is an anti-VEGF aptamer (e.g., EYE001). For anti-VEGF aptamers, see, e.g., Ng et al. (2006) *Nature Reviews Drug Discovery* 5:123; and U.S. Pat. Nos. 6,426,335; 6,168,778; 6,147,204; 6,051,698; and 6,011,020. For example, an aptamer directed against $VEGF_{165}$, the isoform primarily responsible for pathological ocular neovascularization and vascular permeability, would be suitable.

Polypeptide Gene Products

Where the gene product is a polypeptide, exemplary polypeptides include neuroprotective polypeptides and anti-angiogenic polypeptides. Suitable polypeptides include, but are not limited to, glial derived neurotrophic factor (GDNF), fibroblast growth factor 2 (FGF-2), nurturin, ciliary neurotrophic factor (CNTF), nerve growth factor (NGF; e.g., nerve growth factor-β), brain derived neurotrophic factor (BDNF), neurotrophin-3 (NT-3), neurotrophin-4 (NT-4), neurotrophin-6 (NT-6), epidermal growth factor (EGF), pigment epithelium derived factor (PEDF), a Wnt polypeptide, soluble Flt-1, angiostatin, endostatin, an anti-VEGF antibody, a soluble VEGFR, and a member of the hedgehog family (sonic hedgehog, indian hedgehog, and desert hedgehog, etc.).

GDNF can be synthesized in cells as a 211-amino acid residue prepropeptide that is processed to yield a dimeric protein composed of two 134-amino acid residue subunits. GDNF has been described amply in the literature; see, e.g., Lin et al. (1993) *Science* 260:1130; Grimm et al. (1998) *Hum. Mol. Genet.* 7:1873; Airaksinen and Saarma (2002) *Nature Reviews* 3:383; and Kyuno and Jones (2007) *Gene Expr. Patterns* 7:313. GDNF amino acid sequences are known; see, e.g., GenBank Accession Nos. NP_000505, NP_001177397; NP_001177398; and NP_954701. Suitable for use herein is a GDNF polypeptide having at least about 85%, at least about 90%, at least about 95%, or 100%, amino acid sequence identity to a contiguous stretch of 134 amino acids of the amino acid sequence of amino acids 78-211 of the sequence set forth in SEQ ID NO:10. Active fragments of GDNF are also suitable for use. In some embodiments, a GDNF polypeptide has a length of from about 75 amino acids (aa) to about 100 aa, from about 100 aa to about 134 aa, from about 134 aa to about 185 aa, from about 185 aa to about 202 aa, from about 202 aa to about 211 aa, or from about 211 aa to about 228 aa.

PEDF is an approximately 418-amino acid polypeptide that exhibits both neurotrophic and anti-angiogenic properties. Steele et al. (1993) *Proc. Natl. Acad. Sci. USA* 90:1526. PEDF amino acid sequences are known; see, e.g., GenBank Accession No. NP_002606; and Steele et al. (1993) supra. A suitable PEDF polypeptide can have at least about 85%, at least about 90%, at least about 95%, or 100%, amino acid sequence identity to a contiguous stretch of from about 25 amino acids (aa) to about 35 aa, from about 35 aa to about 45 aa, from about 45 aa to about 50 aa, from about 50 aa to about 100 aa, from about 100 aa to about 200 aa, from about 200 aa to about 300 aa, from about 300 aa to about 400 aa, or from about 400 aa to 418 aa, of the amino acid sequence set forth in SEQ ID NO:11. In some cases, the PEDF polypeptide is an active fragment. For example, a fragment comprising amino acids 24-57 can exhibit anti-angiogenic properties (see, e.g., Amaral and Becerra (2010) *Invest. Ophthalmol. Vis. Sci.* 51:1318); and a fragment comprising amino acids 58-101 can exhibit neurotrophic properties (see, e.g., Filleur et al. (2005) *Cancer Res.* 65:5144).

Anti-angiogenic polypeptides include, e.g., vascular endothelial growth factor (VEGF) antagonists. Suitable VEGF antagonists include, but are not limited to, inhibitors of VEGFR1 tyrosine kinase activity; inhibitors of VEGFR2 tyrosine kinase activity; an antibody to VEGF; an antibody to VEGFR1; an antibody to VEGFR2; a soluble VEGFR; and the like. See, e.g., Takayama et al. (2000) *Cancer Res.* 60:2169-2177; Mori et al. (2000) *Gene Ther.* 7:1027-1033; and Mahasreshti et al. (2001) *Clin. Cancer Res.* 7:2057-2066; and U.S. Patent Publication No. 20030181377. Antibodies specific for VEGF include, e.g., bevacizumab (AVASTIN™) and ranibizumab (also known as rhuFAb V2). Also suitable for use are anti-angiogenic polypeptides such as endostatin, PEDF, and angiostatin.

Anti-angiogenic polypeptides include, e.g., recombinant polypeptides comprising VEGF receptors. For example, a suitable anti-angiogenic polypeptide would be the soluble form of the VEGFR-1, known as sFlt-1 (Kendall et al. (1996) *Biochem. Biophys. Res. Commun.* 226:324). Suitable anti-angiogenic polypeptides include an immunoglobulin-like (Ig) domain 2 of a first VEGF receptor (e.g., Flt1), alone or in combination with an Ig domain 3 of a second VEGF receptor (e.g., Flk1 or Flt4); the anti-angiogenic polypeptide can also include a stabilization and/or a multimerization component. Such recombinant anti-angiogenic polypeptides are described in, e.g., U.S. Pat. No. 7,521,049.

Anti-VEGF antibodies that are suitable as heterologous gene products include single chain Fv (scFv) antibodies. See, e.g., U.S. Pat. Nos. 7,758,859; and 7,740,844, for anti-VEGF antibodies.

Structural Features

A subject rAAV virion can comprise a variant AAV capsid protein that differs in amino acid sequence by at least one amino acid from a wild-type capsid protein. The amino acid difference(s) can be located in a solvent accessible site in the capsid, e.g., a solvent-accessible loop. For example, the amino acid substitution(s) can be located in a GH loop in the AAV capsid protein. In some cases, the variant capsid protein comprises an amino acid substitution at amino acid 451 and/or 532, compared to the amino acid sequence of AAV6 capsid (SEQ ID NO:1), or the corresponding amino acid in a serotype other than AAV6. In some cases, the variant capsid protein comprises an amino acid substitution at amino acid 319 and/or 451 and/or 532 and/or 642, compared to the amino acid sequence of AAV6 capsid (SEQ ID NO:1), or the corresponding amino acid in a serotype other than AAV6. In some cases, the variant capsid protein comprises one or more of the following substitutions compared to the amino acid sequence of AAV6 capsid (SEQ ID NO:1): I319V, N451D, D532N, and H642N.

Figure 8C:
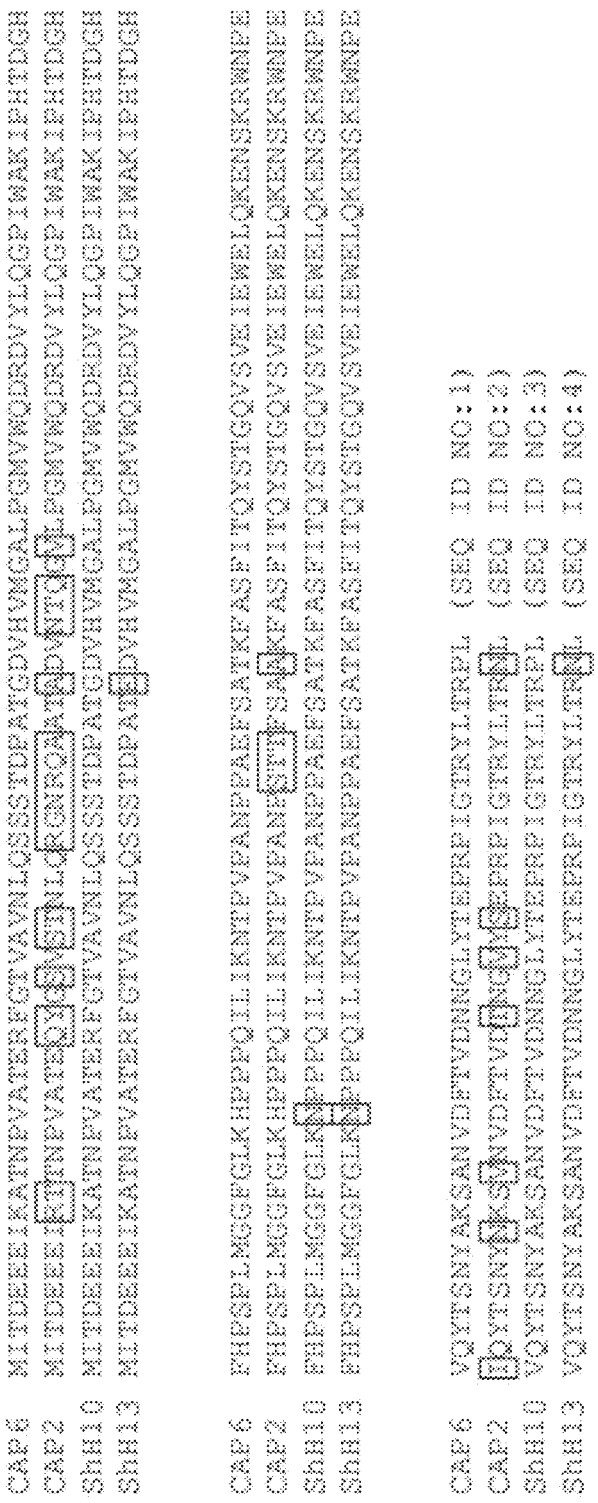

A subject rAAV virion can comprise a variant AAV capsid protein that comprises an amino acid sequence having at least about 85%, at least about 90%, at least about 95%, at least about 98%, at least about 99%, or 100%, amino acid sequence identity to the ShH10 amino acid sequence depicted in FIGS. 8A-C and SEQ ID NO:3, where the variant AAV capsid protein comprises from 1 to about 10 amino acid differences (e.g., amino acid substitutions and/or amino acid insertions and/or amino acid deletions) compared to the AAV6 capsid protein depicted in FIGS. 8A-C and SEQ ID NO:1. The amino acid difference(s) can be located in a solvent accessible site in the capsid, e.g., a solvent-accessible loop. For example, the amino acid substitution(s) can be located in a GH loop in the AAV capsid protein. In some cases, the variant capsid protein comprises an I319V substitution, an N451D substitution, a D532N substitution, and an H642N substitution compared to the amino acid sequence of AAV6 capsid (SEQ ID NO:1).

For example, the variant capsid protein can comprise an amino acid sequence having at least about 85%, at least about 90%, at least about 95%, at least about 98%, at least about 99%, or 100%, amino acid sequence identity to the ShH10 amino acid sequence depicted in SEQ ID NO:3, where the variant capsid protein an I319V substitution, an N451D substitution, a D532N substitution, and an H642N substitution compared to the amino acid sequence of AAV6 capsid (SEQ ID NO:1).

In some embodiments, the variant capsid protein can comprise an amino acid sequence that has at least about 95%, at least about 98%, at least about 99%, or 100%, amino acid sequence identity to the ShH10 amino acid sequence depicted in FIGS. 8A-C and SEQ ID NO:3, and that includes an I319V substitution, relative to AAV6 capsid. For example, the variant capsid protein can comprise an amino acid sequence that has at least about 95%, at least about 98%, at least about 99%, or 100%, amino acid sequence identity to the ShH10 amino acid sequence set forth in SEQ ID NO:8 (comprising an I319V substitution compared to SEQ ID NO:1).

In some embodiments, the variant capsid protein can comprise an amino acid sequence that has at least about 95%, at least about 98%, at least about 99%, or 100%, amino acid sequence identity to the ShH10 amino acid sequence depicted in FIGS. 8A-C and SEQ ID NO:3, and that includes an I319V substitution and an N451D substitution, relative to AAV6 capsid. For example, the variant capsid protein can comprise an amino acid sequence that has at least about 95%, at least about 98%, at least about 99%, or 100%, amino acid sequence identity to the ShH10 amino acid sequence set forth in SEQ ID NO:6 (comprising an I319V and an N451D substitution compared to SEQ ID NO:1).

In some embodiments, the variant capsid protein can comprise an amino acid sequence that has at least about 95%, at least about 98%, at least about 99%, or 100%, amino acid sequence identity to the ShH10 amino acid sequence depicted in FIGS. 8A-C and SEQ ID NO:3, and that includes an I319V substitution and a D532N substitution, relative to AAV6 capsid. For example, the variant capsid protein can comprise an amino acid sequence that has at least about 95%, at least about 98%, at least about 99%, or 100%, amino acid sequence identity to the ShH10 amino acid sequence set forth in SEQ ID NO:9 (comprising an I319V and a D532N substitution compared to SEQ ID NO:1).

In some embodiments, the variant capsid protein can comprise an amino acid sequence that has at least about 95%, at least about 98%, at least about 99%, or 100%, amino acid sequence identity to the ShH10 amino acid sequence depicted in FIGS. 8A-C and SEQ ID NO:3, and that includes an N451D substitution and a D532N substitution, relative to AAV6 capsid. For example, the variant capsid protein can comprise an amino acid sequence that has at least about 95%, at least about 98%, at least about 99%, or 100%, amino acid sequence identity to the ShH10 amino acid sequence set forth in SEQ ID NO:7 (comprising an N451D and a D532N substitution compared to SEQ ID NO:1).

In some embodiments, the variant capsid protein can comprise an amino acid sequence that has at least about 95%, at least about 98%, at least about 99%, or 100%, amino acid sequence identity to the ShH10 amino acid sequence depicted in FIGS. 8A-C and SEQ ID NO:3, and that includes an I319V substitution, an N451D substitution, and a D532N substitution, relative to AAV6 capsid. For example, the variant capsid protein can comprise an amino acid sequence that has at least about 95%, at least about 98%, at least about 99%, or 100%, amino acid sequence identity to the ShH10 amino acid sequence set forth in SEQ ID NO:5 (comprising an I319V, an N451D, and a D532N substitution compared to SEQ ID NO:1).

Control Elements

The heterologous nucleotide sequence can be operably linked to control elements that direct the transcription or expression thereof in the nucleotide sequence in vivo. Such control elements can comprise control sequences normally associated with the selected gene (e.g., endogenous cellular control elements). Alternatively, heterologous control sequences can be employed. Useful heterologous control sequences generally include those derived from sequences encoding mammalian or viral genes. Examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter that is heterologous to the gene of interest, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, can also be used. Such promoter sequences are commercially available from, e.g., Stratagene (San Diego, Calif.).

In some embodiments, a cell type-specific or a tissue-specific promoter will be operably linked to the heterologous nucleic acid encoding the heterologous gene product, such that the gene product is produced selectively or preferentially in a particular cell type(s) or tissue(s). In some embodiments, an inducible promoter will be operably linked to the heterologous nucleic acid.

Methods for Generating an rAAV Virion

An AAV expression vector which comprises a heterologous nucleic acid and which is used to generate an rAAV virion, can be constructed using methods that are well known in the art. See, e.g., Koerber et al. (2009) Mol. Ther. 17:2088; Koerber et al. (2008) Mol Ther, 16: 1703-1709: U.S. Pat. Nos. 7,439,065, 6,951,758, and 6,491,907. For example, the heterologous sequence(s) can be directly inserted into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Curr. Topics Microbiol. Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

In order to produce rAAV virions, an AAV expression vector is introduced into a suitable host cell using known techniques, such as by transfection. A number of transfection techniques are generally known in the art. See, e.g., Graham et al. (1973) Virology, 52:456, Sambrook et al. (1989) Molecular Cloning, A Laboratory Manual, Cold Spring Harbor Laboratories, New York, Davis et al. (1986) Basic Methods in Molecular Biology, Elsevier, and Chu et al. (1981) Gene 13:197. Particularly suitable transfection methods include calcium phosphate co-precipitation (Graham et al. (1973) Virol. 52:456-467), direct micro-injection into cultured cells (Capecchi, M. R. (1980) Cell 22:479-488), electroporation (Shigekawa et al. (1988) BioTechniques 6:742-751), liposome mediated gene transfer (Mannino et al. (1988) BioTechniques 6:682-690), lipid-mediated transduction (Felgner et al. (1987) Proc. Natl. Acad. Sci. USA 84:7413-7417), and nucleic acid delivery using high-velocity microprojectiles (Klein et al. (1987) Nature 327:70-73).

Suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used. For example, the human cell line 293 is a human embryonic kidney cell line that has been transformed with adenovirus type-5 DNA fragments (Graham et al. (1977) J. Gen. Virol. 36:59), and expresses the adenoviral E1a and E1b genes (Aiello et al. (1979) Virology 94:460). The 293 cell line is readily transfected, and provides a convenient platform in which to produce rAAV virions.

Methods of producing an AAV virion in insect cells are known in the art, and can be used to produce a subject rAAV virion. See, e.g., U.S. Patent Publication No. 2009/0203071; U.S. Pat. No. 7,271,002; and Chen (2008) *Mol. Ther.* 16:924.

Pharmaceutical Compositions

The present disclosure provides a pharmaceutical composition comprising: a) a subject rAAV virion, as described above; and b) a pharmaceutically acceptable carrier, diluent, excipient, or buffer. In some embodiments, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A subject composition can comprise a liquid comprising a subject rAAV virion in solution, in suspension, or both. As used herein, liquid compositions include gels. In some cases, the liquid composition is aqueous. In some embodiments, the composition is an in situ gellable aqueous composition, e.g., an in situ gellable aqueous solution. Aqueous compositions have ophthalmically compatible pH and osmolality.

Methods of Delivering a Gene Product to a Retinal Cell

The present disclosure provides a method of delivering a gene product to a retinal cell (e.g., a Müller cell) in an individual, the method comprising administering to the individual a subject rAAV virion as described above. The methods generally involve introducing a subject rAAV virion into the eye of an individual, where the rAAV virion enters a retinal cell (e.g., a Müller cell) in the eye of the individual, and where the gene product encoded by the heterologous polynucleotide present in the rAAV virion is produced in the retinal cell. The eye can be one that has impaired vision and/or that has an ocular disease. The eye can be one that is at elevated risk of developing impaired vision and/or an ocular disease. Introduction of a subject rAAV virion into the eye of an individual can be carried out by intraocular injection, by intravitreal injection, by intravitreal implant, subretinal injection, suprachoroidal administration, intravenous administration, or by any other convenient mode or route of administration.

In some cases, a subject rAAV virion, when introduced (e.g., via intravitreal injection) into an eye of an individual, provides for high level production of the heterologous gene product encoded by the rAAV in the eye. For example, a heterologous polypeptide encoded by the rAAV can be produced in the eye at a level of from about 1 µg to about 50 µg, or greater than 50 µg. As another example, a heterologous polypeptide encoded by the rAAV can be produced in the vitreous fluid of the eye at a level of from about 100 pg/mL to about 5000 pg/mL vitreous fluid, e.g., from about 100 pg/mL to about 500 pg/mL, from about 500 pg/mL to about 1000 pg/mL, from about 1000 pg/mL to about 2000 pg/mL, from about 2000 pg/mL to about 3000 pg/mL, from about 3000 pg/mL to about 4000 pg/mL, or from about 4000 pg/mL to about 5000 pg/mL. In some cases, a polypeptide encoded by the rAAV can be produced in the vitreous fluid of the eye at a level of greater than 5000 pg/mL vitreous fluid.

In some cases, a subject rAAV virion, when introduced (e.g., via intravitreal injection) into an eye of an individual, provides for production of the heterologous gene product encoded by the rAAV in at least about 10%, at least about 15%, at least about 20%, at least about 25%, at least about 30%, at least about 35%, at least about 40%, at least about 50% at least about 60%, at least about 70%, at least about 80%, or more than 80%, of the Müller cells in the eye.

In some embodiments, a subject rAAV virion, when introduced (e.g., via intravitreal injection) into an eye of an individual, provides for production of the heterologous gene product encoded by the rAAV for a period of time of from about 2 days to about 6 months, e.g., from about 2 days to about 7 days, from about 1 week to about 4 weeks, from about 1 month to about 2 months, or from about 2 months to about 6 months. In some embodiments, a subject rAAV virion, when introduced (e.g., via intravitreal injection) into an eye of an individual, provides for production of the heterologous gene product encoded by the rAAV for a period of time of more than 6 months, e.g., from about 6 months to 20 years or more, or greater than 1 year, e.g., from about 6 months to about 1 year, from about 1 year to about 2 years, from about 2 years to about 5 years, from about 5 years to about 10 years, from about 10 years to about 15 years, from about 15 years to about 20 years, or more than 20 years.

The gene product can be a polypeptide or a nucleic acid. Nucleic acid gene products include, e.g., an interfering RNA (e.g., an shRNA, an siRNA, and the like), a ribozyme, an antisense RNA, and an aptamer, as described above.

Where the gene product is an interfering RNA (RNAi), suitable RNAi include RNAi that decrease the level of an angiogenic factor in a cell. For example, an RNAi can be an shRNA or siRNA that reduces the level of VEGF in a cell. RNAi agents that target VEGF include, e.g., an RNAi described in U.S. Patent Publication No. 2011/0224282. For example, an siRNA specific for VEGF-A, VEGFR1, or VEGFR2 would be suitable. Suitable nucleic acid gene products also include a ribozyme specific for VEGF-A, VEGFR1, or VEGFR2; an antisense specific for VEGF-A, VEGFR1, or VEGFR2; siRNA specific for VEGF-A, VEGFR1, or VEGFR2; etc.

Also suitable as a gene product is an miRNA that reduces the level of VEGF by regulating VEGF gene expression, e.g., through post-transcriptional repression or mRNA degradation. Examples of suitable miRNA include, e.g., miR-15b, miR-16, miR-20a, and miR-20b. See, e.g., Hua et al. (2006) *PLoS ONE* 1:e116.

Also suitable is an anti-VEGF aptamer (e.g., EYE001). For anti-VEGF aptamers, see, e.g., Ng et al. (2006) *Nature Reviews Drug Discovery* 5:123; and U.S. Pat. Nos. 6,426, 335; 6,168,778; 6,147,204; 6,051,698; and 6,011,020. For example, an aptamer directed against $VEGF_{165}$, the isoform primarily responsible for pathological ocular neovascularization and vascular permeability, would be suitable.

Where the gene product is a polypeptide, exemplary polypeptides include neuroprotective polypeptides and anti-angiogenic polypeptides. Suitable polypeptides include, but are not limited to, glial derived neurotrophic factor (GDNF), fibroblast growth factor 2 (FGF-2), nurturin, ciliary neurotrophic factor (CNTF), nerve growth factor (NGF; e.g., nerve growth factor-β), brain derived neurotrophic factor (BDNF), neurotrophin-3 (NT-3), neurotrophin-4 (NT-4), neurotrophin-6 (NT-6), epidermal growth factor (EGF), pigment epithelium derived factor (PEDF), a Wnt polypeptide, and a member of the hedgehog family (sonic hedgehog, indian hedgehog, and desert hedgehog, etc.).

GDNF can be synthesized in cells as a 211-amino acid residue prepropeptide that is processed to yield a dimeric protein composed of two 134-amino acid residue subunits. GDNF has been described amply in the literature; see, e.g., Lin et al. (1993) *Science* 260:1130; Grimm et al. (1998) *Hum. Mol. Genet.* 7:1873; Airaksinen and Saarma (2002) *Nature Reviews* 3:383; and Kyuno and Jones (2007) *Gene Expr. Patterns* 7:313. GDNF amino acid sequences are known; see, e.g., GenBank Accession Nos. NP_000505, NP_001177397; NP_001177398; and NP_954701. Suitable for use herein is a GDNF polypeptide having at least about 85%, at least about 90%, at least about 95%, or 100%, amino acid sequence identity to a contiguous stretch of 134 amino acids of the amino acid sequence of amino acids 78-211 of the sequence set forth in SEQ ID NO:10. Active fragments of GDNF are also suitable for use. In some embodiments, a GDNF polypeptide has a length of from about 75 amino acids (aa) to about 100 aa, from about 100 aa to about 134 aa, from about 134 aa to about 185 aa, from about 185 aa to about 202 aa, from about 202 aa to about 211 aa, or from about 211 aa to about 228 aa.

PEDF is an approximately 418-amino acid polypeptide that exhibits both neurotrophic and anti-angiogenic properties. Steele et al. (1993) *Proc. Natl. Acad. Sci. USA* 90:1526. PEDF amino acid sequences are known; see, e.g., GenBank Accession No. NP_002606; and Steele et al. (1993) supra. A suitable PEDF polypeptide can have at least about 85%, at least about 90%, at least about 95%, or 100%, amino acid sequence identity to a contiguous stretch of from about 25 amino acids (aa) to about 35 aa, from about 35 aa to about 45 aa, from about 45 aa to about 50 aa, from about 50 aa to about 100 aa, from about 100 aa to about 200 aa, from about 200 aa to about 300 aa, from about 300 aa to about 400 aa, or from about 400 aa to 418 aa, of the amino acid sequence set forth in SEQ ID NO:11. In some cases, the PEDF polypeptide is an active fragment. For example, a fragment comprising amino acids 24-57 can exhibit anti-angiogenic properties (see, e.g., Amaral and Becerra (2010) *Invest. Ophthalmol. Vis. Sci.* 51:1318); and a fragment comprising amino acids 58-101 can exhibit neurotrophic properties (see, e.g., Filleur et al. (2005) *Cancer Res.* 65:5144).

Anti-angiogenic polypeptides include, e.g., vascular endothelial growth factor (VEGF) antagonists. Suitable VEGF antagonists include, but are not limited to, inhibitors of VEGFR1 tyrosine kinase activity; inhibitors of VEGFR2 tyrosine kinase activity; an antibody to VEGF; an antibody to VEGFR1; an antibody to VEGFR2; a soluble VEGFR; and the like. See, e.g., Takayama et al. (2000) *Cancer Res.* 60:2169-2177; Mori et al. (2000) *Gene Ther.* 7:1027-1033; and Mahasreshti et al. (2001) *Clin. Cancer Res.* 7:2057-2066; and U.S. Patent Publication No. 20030181377. Antibodies specific for VEGF include, e.g., bevacizumab (AVASTIN™) and ranibizumab (also known as rhuFAb V2). Also suitable for use are anti-angiogenic polypeptides such as endostatin, PEDF, and angiostatin.

Anti-angiogenic polypeptides include, e.g., recombinant polypeptides comprising VEGF receptors. For example, a suitable anti-angiogenic polypeptide would be the soluble form of the VEGFR-1, known as sFlt-1 (Kendall et al. (1996) *Biochem. Biophys. Res. Commun.* 226:324). Suitable anti-angiogenic polypeptides include an immunoglobulin-like (Ig) domain 2 of a first VEGF receptor (e.g., Flt1), alone or in combination with an Ig domain 3 of a second VEGF receptor (e.g., Flk1 or Flt4); the anti-angiogenic polypeptide can also include a stabilization and/or a multimerization component. Such recombinant anti-angiogenic polypeptides are described in, e.g., U.S. Pat. No. 7,521,049.

Anti-VEGF antibodies that are suitable as heterologous gene products include single chain Fv (scFv) antibodies. See, e.g., U.S. Pat. Nos. 7,758,859; and 7,740,844, for anti-VEGF antibodies.

Method of Treating a Retinal Disease

The present disclosure provides a method of treating a retinal disease, the method comprising administering to an individual in need thereof an effective amount of a subject rAAV virion as described above. A subject rAAV virion can be administered via intraocular injection, by intravitreal injection, by intravitreal implant, or by any other convenient mode or route of administration.

A "therapeutically effective amount" will fall in a relatively broad range that can be determined through experimentation and/or clinical trials. For example, for in vivo injection, e.g., injection directly into the eye, a therapeutically effective dose will be on the order of from about $10^6$ to about $10^{15}$ of the rAAV virions, e.g., from about $10^8$ to $10^{12}$ rAAV virions. For example, for in vivo injection, e.g., injection directly into the eye, a therapeutically effective dose will be on the order of from about $10^6$ to about $10^{15}$ infectious units, e.g., from about $10^8$ to about $10^{12}$ infectious units. Other effective dosages can be readily established by one of ordinary skill in the art through routine trials establishing dose response curves.

In some cases, a therapeutically effective amount of a subject rAAV virion is an amount that, when administered to an individual (e.g., administered via intravitreal injection into an eye (e.g., a visually impaired eye; an eye having an ocular disease; an eye that is at risk of developing an ocular disease) of the individual) in one or more doses, is effective to slow the progression of retinal degeneration in the individual. For example, a therapeutically effective amount of a subject rAAV virion can be an amount that, when administered to an individual (e.g., administered via intravitreal injection to an individual) in one or more doses, is effective to slow the progression of retinal degeneration by at least about 15%, at least about 20%, at least about 25%, at least about 30%, at least about 40%, at least about 50%, at least about 60%, at least about 70%, at least about 80%, or more than 80%, compared to the progression of retinal degeneration in the absence of treatment with the rAAV virion.

In some cases, a therapeutically effective amount of a subject rAAV virion is an amount that, when administered to an individual (e.g., administered via intravitreal injection into an eye of the individual) in one or more doses, is effective to improve vision in the individual. For example, a therapeutically effective amount of a subject rAAV virion can be an amount that, when administered to an individual (e.g., administered via intravitreal injection into an eye of the individual) in one or more doses, is effective to improve vision by at least about 15%, at least about 20%, at least about 25%, at least about 30%, at least about 40%, at least about 50%, at least about 60%, at least about 70%, at least about 80%, or more than 80%, compared to the individual's vision in the absence of treatment with the rAAV virion.

In some cases, a therapeutically effective amount of a subject rAAV virion is an amount that, when administered to an individual (e.g., administered via intravitreal injection into an eye of the individual) in one or more doses, is effective to decrease the rate of vision loss in an eye with impaired vision.

Improvement of clinical symptoms are monitored by one or more methods known to the art, for example, tests of functional vision, such as visual acuity, visual field, contrast sensitivity, color vision, mobility, and light sensitivity. Clinical symptoms may also be monitored by anatomical or physiological means, such as indirect ophthalmoscopy, fundus photography, fluorescein angiopathy, optical coherence tomography, electroretinography (full-field, multifocal, or other), external eye examination, slit lamp biomicroscopy, applanation tonometry, pachymetry, autorefaction, or other measures of functional vision.

Multiple doses of a subject rAAV virion can be administered to an individual in need thereof. Where multiple doses are administered over a period of time, an active agent is administered once a month to about once a year, from about once a year to once every 2 years, from about once every 2 years to once every 5 years, or from about once every 5 years to about once every 10 years, over a period of time. For example, a subject rAAV virion is administered over a period of from about 3 months to about 2 years, from about 2 years to about 5 years, from about 5 years to about 10 years, from about 10 years to about 20 years, or more than 20 years. The actual frequency of administration, and the actual duration of treatment, depends on various factors.

As an example, a subject method of treating an ocular disorder can include administering an initial dose of a subject rAAV virion; and administering at least a second dose (a subsequent dose) of the rAAV virion. Where two or more subsequent doses are administered, the subsequent dose(s) can be separated in time from each other by at least one month, at least 3 to 6 months, at least 6 months to 1 year, at least 1 year to 5 years, at least 5 years to 10 years, at least 10 years to 20 years, or more than 20 years.

Ocular diseases that can be treated or prevented using a subject method include, but are not limited to, selected from acute macular neuroretinopathy; macular telangiectasia; Behcet's disease; choroidal neovascularization; diabetic uveitis; histoplasmosis; macular degeneration, such as acute macular degeneration, Scorsby's macular dystrophy, early or intermediate (dry) macular degeneration, or a form of advanced macular degeneration, such as exudative macular degeneration or geographic atrophy; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative and non-proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy; epiretinal membrane disorders; central or branch retinal vein occlusion; anterior ischemic optic neuropathy, non-retinopathy diabetic retinal dysfunction; retinitis pigmentosa; retinoschisis; and glaucoma.

Subjects Suitable for Treatment

Subjects suitable for treatment according to a method of the present disclosure include individuals having an ocular disease, as described above. Subjects suitable for treatment also include individuals at increased risk (e.g., at increased risk relative to the general population) of developing an ocular disease. Ocular diseases include those listed above.

Nucleic Acids and Host Cells

The present disclosure provides an isolated nucleic acid comprising a nucleotide sequence that encodes a variant adeno-associated virus (AAV) capsid protein, where the variant AAV capsid protein comprises an amino acid sequence having at least about 85% at least about 90%, at least about 95%, at least about 98%, at least about 99%, or 100%, amino acid sequence identity to the ShH10 amino acid sequence depicted in FIGS. 8A-C, where the AAV capsid protein does not comprise an amino acid sequence present in a naturally occurring AAV capsid protein, and where the variant capsid protein, when present in an AAV virion, provides for increased infectivity of the AAV virion for a retinal cell.

The present invention further provides host cells, e.g., isolated (genetically modified) host cells, comprising a subject nucleic acid. A subject host cell can be an isolated cell, e.g., a cell in in vitro culture. A subject host cell is useful for producing a subject rAAV virion, as described below. Where a subject host cell is used to produce a subject rAAV virion, it is referred to as a "packaging cell." In some embodiments, a subject host cell is stably genetically modified with a subject nucleic acid. In other embodiments, a subject host cell is transiently genetically modified with a subject nucleic acid.

A subject nucleic acid is introduced stably or transiently into a host cell, using established techniques, including, but not limited to, electroporation, calcium phosphate precipitation, liposome-mediated transfection, baculovirus infection, and the like. For stable transformation, a subject nucleic acid will generally further include a selectable marker, e.g., any of several well-known selectable markers such as neomycin resistance, and the like.

A subject host cell is generated by introducing a subject nucleic acid into any of a variety of cells, e.g., mammalian cells, including, e.g., murine cells, and primate cells (e.g., human cells). Suitable mammalian cells include, but are not limited to, primary cells and cell lines, where suitable cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), Sf9 cells, human embryonic kidney (HEK) cells (ATCC No. CRL1573), HLHepG2 cells, and the like.

In some embodiments, a subject genetically modified host cell includes, in addition to a nucleic acid comprising a nucleotide sequence encoding a variant AAV capsid protein, as described above, a nucleic acid that comprises a nucleotide sequence encoding one or more AAV rep proteins. In other embodiments, a subject host cell further comprises an rAAV vector. An rAAV virion can be generated using a subject host cell. Methods of generating an rAAV virion are described in, e.g., U.S. Patent Publication No. 2005/0053922 and U.S. Patent Publication No. 2009/0202490.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Generation of rAAV Virions with Variant Capsids and Exhibiting Increased Infectivity of Müller Glial Cells Materials and Methods
Generation of rAAV Vectors Vectors were produced by the plasmid co-transfection method (Koerber et al. (2009) *Mol. Ther.* 17:2088), and the resulting lysates were purified via iodixanol gradient ultracentrifugation as previously described. Koerber et al. *Mol Ther.* 2008; 16:1703-1709. This fraction was then passed through a heparin column, which was washed with 5 mL phosphate-buffered saline (PBS) and eluted with 5 mL of a 1 M NaCl solution. The resulting viral fractions were desalted and concentrated with Amicon Ultra-15 Centrifugal Filter Units to a final volume of 200 µl. Vector was then titered for DNase-resistant vector genomes by real time polymerase chain reaction (PCR) relative to a standard.
Intraocular Administration Routes Adult wild type Sprague Dawley rats were used for the studies discussed in this Example. All animal procedures were conducted according to the ARVO Statement for the Use of Animals and the guidelines of the Office of Laboratory Animal Care at the University of California, Berkeley. Before vector administration, rats were anesthetized with ketamine (72 mg/kg) and xylazine (64 mg/kg) by intraperitoneal injection. An ultrafine 30½-gauge disposable needle was passed through the sclera, at the equator and next to the limbus, into the vitreous cavity. Injection of 5 µl, containing $1-5 \times 10^{12}$ vg/ml of AAV dsCAG-green fluorescent protein (GFP), was made with direct observation of the needle in the center of the vitreous cavity.
Fundus Photography Fundus imaging was performed one to eight weeks after injection with a fundus camera (Retcam II; Clarity Medical Systems Inc., Pleasanton, Calif.) equipped with a wide angle 130° retinopathy of prematurity (ROP) lens to monitor eGFP expression in live, anesthetized rats. Pupils were dilated for fundus imaging with phenylephrine (2.5%) and atropine sulfate (1%).
Cryosections One to eight weeks after vector injection, rats were humanely euthanized, the eyes were enucleated, a hole was introduced in the cornea, and tissue was fixed with 10% neutral buffered formalin for 2-3 hours. The cornea and lens were removed. The eyecups were washed in PBS followed by 30% sucrose in the same buffer overnight. Eyes were then embedded in optimal cutting temperature embedding compound (OCT; Miles Diagnostics, Elkhart, Ind.) and oriented for 10 µm thick transverse retinal sections.

Immunolabeling and Histological Analysis

Tissue sections were rehydrated in PBS for 5 min, followed by incubation in a blocking solution of 1% bovine serum albumin (BSA), 0.5% Triton X-100, and 2% normal donkey serum in PBS for 2-3 hours. Slides were then incubated with commercial monoclonal antibodies raised against glutamine synthetase in rabbit (Sigma G2781) at a 1:3000 dilution, calbindin (Abcam ab11426-50) in rabbit at a 1:1000 dilution, vimentin in mouse (Dako M0725) at a 1:1000 dilution, or laminin in rabbit (Sigma, L9393) at 1:100 in blocking solution, overnight at 4° C.

The sections were then incubated with Cy3-conjugated secondary anti-rabbit or anti-mouse antibody (Molecular Probes) at a 1:1000 dilution in blocking solution for 2 hours at room temperature. The results were examined by fluorescence microscopy using an Axiophot microscope (Zeiss, Thornwood, N.Y.) equipped with a Xcite PC200 light source and QCapturePro camera or a confocal microscope (LSM5; Carl Zeiss Microimaging). Transduction profiles were analyzed by counting individual cells from whole retinas in 15 µm cryosections (n=6) using fluorescence microscopy. Efficiencies were calculated by dividing the total number of these transduced Müller cells by the total number of Müller cells in the retinal slice (mm) in which these cells were present (n=6).
In Vitro Transduction Analysis Transduction studies using rAAV CMV-GFP (GFP operably linked to a cytomegalovirus promoter) were performed with $5 \times 10^4$ cells (CHO, pgsA, Pro5, and Lec1) in 12-well plates. Cells were transduced with rAAV GFP vectors at a genomic multiplicity of infection (gMOI) of $10^3$-$10^5$ (n=3), and the percentage of GFP-expressing cells was determined by flow cytometry 48 hours post-infection.
Results
In Vivo Characterization of Müller Cell Permissive Variants Several novel AAV capsids were recently evolved, that efficiently transduced both primary human astrocytes in vitro and rat astrocytes in vivo using highly diverse AAV libraries ($>10^7$). Koerber et al. (2009) supra. These variants were generated via multiple evolutionary rounds (i.e. diversification followed by positive selection for enhanced astrocyte transduction in vitro) with several distinct libraries: (1) an AAV2 random mutagenesis library generated via error prone PCR (Maheshri et al. *Nat Biotechnol.* 2006; 24:198-204), (2) a random chimera AAV library generated by shuffling the cap genes of 7 natural human and non-human AAV serotypes (Koerber et al. *Mol Ther.* 2008; 16:1703-1709), and (3) a novel AAV2 library with surface-exposed loops of the capsid library diversified based on a bioinformatics approach. Koerber et al. (2009) supra.

Figure 2:
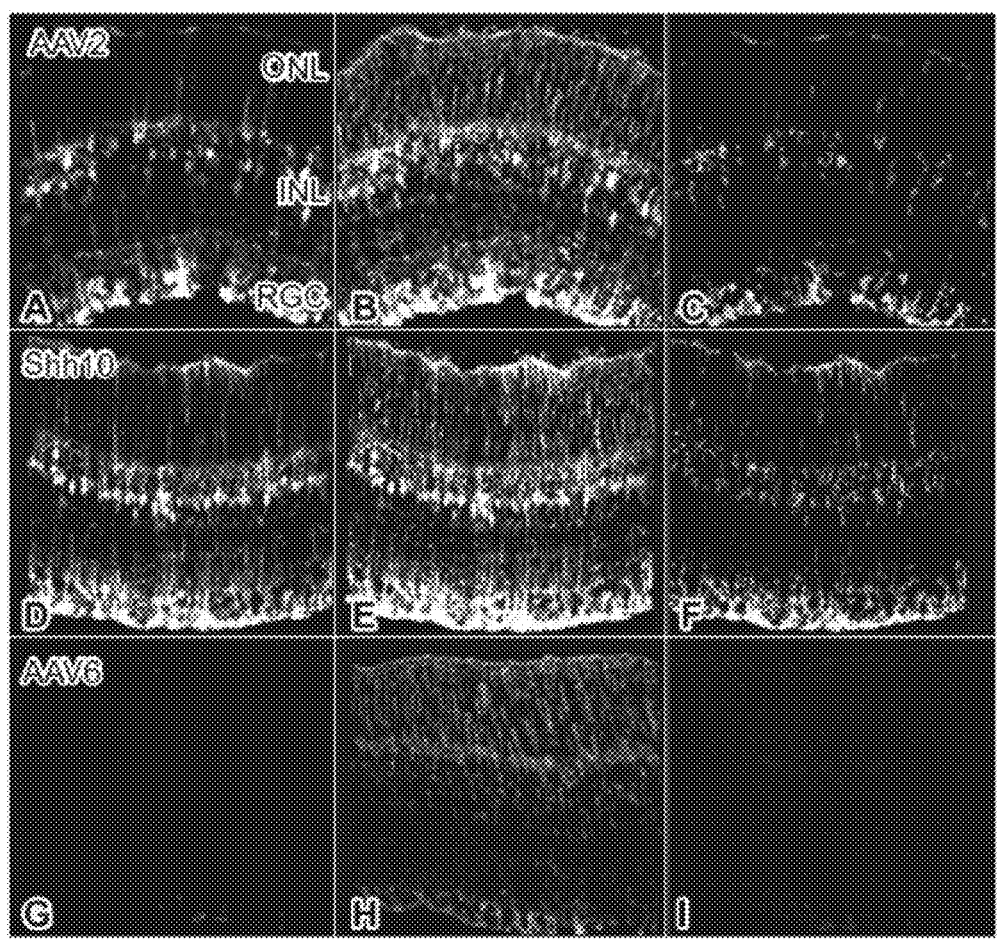
FIGS. 2A-I depict rShH10 expression following intravitreal injection in adult rat retina.
Figure 3:
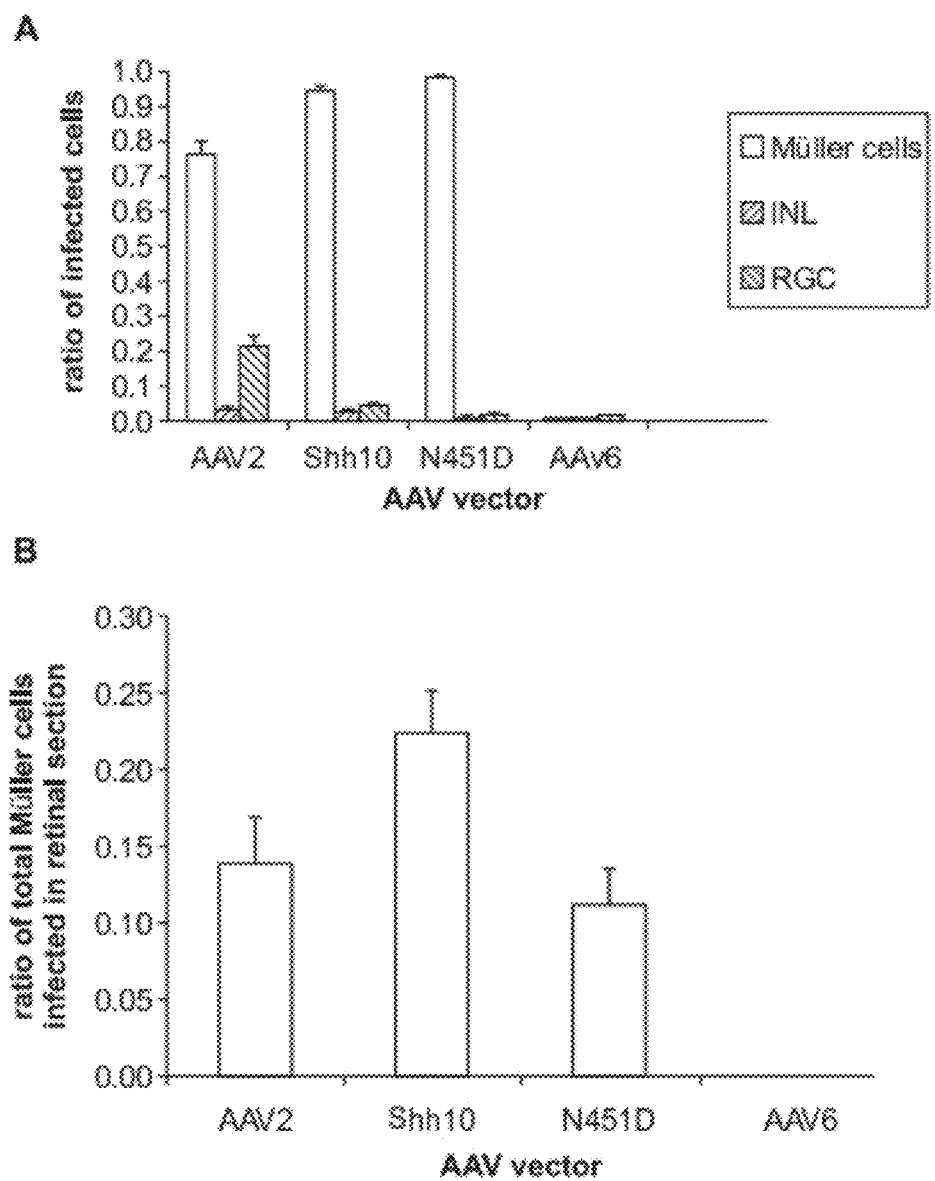
FIGS. 3A and 3B depict transduction specificity and efficiency of ShH10.

The utility of these variants was explored for intravitreal transduction of Müller cells. Here, the eight isolated mutants that demonstrated the greatest in vitro astrocyte infectivity (FIG. 8) were individually analyzed for the ability to transduce the retina from the vitreous using double-stranded (ds) AAV CAG-GFP vectors purified via iodixanol gradient ultracentrifugation and heparin affinity chromatography. Intravitreal injections of $2.5 \times 10^{10}$ genomic particles revealed one previously unreported variant named ShH10, derived from an AAV6 parent serotype from the shuffled (ShH) library, that showed a dramatic increase in specificity and efficiency for Müller cells relative to controls at three weeks post-injection (FIGS. 2 and 3). Interestingly, no other mutants demonstrated visible expression as determined by GFP fundus imaging and immunohistochemistry. Recombinant ShH10 (rShH10) led to diffuse expression throughout the retina with a highly specific transduction profile of approximately 94% Müller cells, 2% interneurons, and 4% retinal ganglion cells (FIGS.

Figure 4:
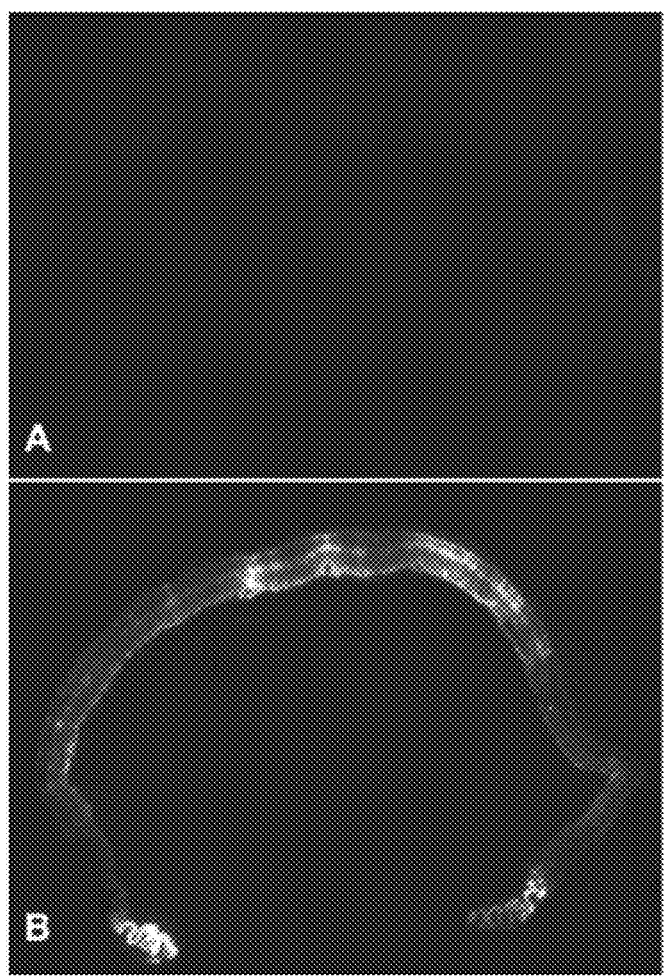
FIGS. 4A and 4B depict rShH10 expression in the whole retina following intravitreal injection.

2, 3, 4). In comparison, the parent vector, AAV6, showed very low transduction of the retina, and the related AAV2 vector showed a less specific retinal tropism with a transduction profile of approximately 76% Müller cells, 3% interneurons, and 21% retinal ganglion cells (FIGS. 2, 3, 4). Quantification of transduction efficiencies revealed that ShH10 was approximately 62% more efficient at infecting Müller cells relative to AAV2, infecting 22% vs. 14% of total Müller cells respectively in transverse retinal slices (FIG. 3B).

Figure 5:
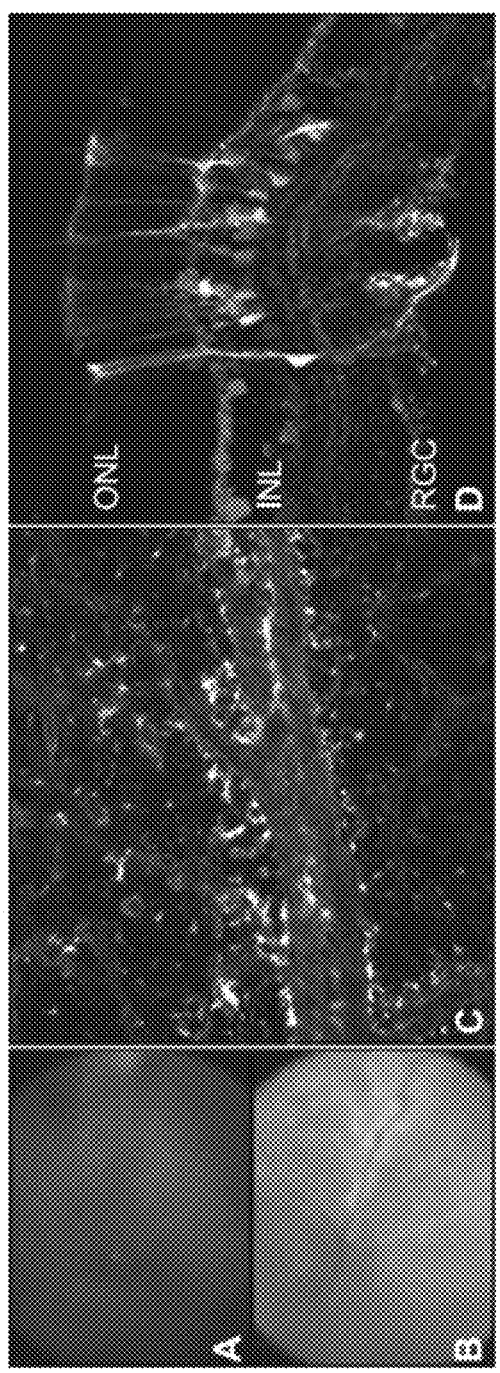
FIGS. 5A-D depict retinal astrocyte infectivity of ShH10.

Temporal observation of ShH10 expression using fundus imaging, coupled with anti-laminin immunostaining of retinal flatmounts to visualize vasculature, also revealed a unique tropism for retinal astrocytes at earlier time points following injection (FIG. 5). Unlike Müller cells, retinal astrocytes are not derived from the retinal neuroepithelium, but serve some analogous roles in the retina including providing nutritional support to neurons, neurotransmitter metabolism, and ionic homeostasis. Trivino et al. *Vision Res.* 1996; 36:2015-2028. They also serve as axonal glial sheaths for ganglion cells bodies and envelop the retinal vasculature, forming part of the blood-brain barrier. One week post-injection, fundus imaging revealed localized expression near those areas dense in retinal astrocytes, e.g. the optic nerve and along retinal vasculature (FIG. 5a)). Additionally, transverse retinal sections showed that areas underlying major vasculature bore strong Müller expression (FIG. 5d). At later time points (2-3 weeks), expression became more evenly spread, but interestingly, those regions in proximity to vasculature ultimately maintained the strongest Müller cell expression (FIG. 4)).

FIG. 1 depicts Müller glia in the retina. Illustration of Müller glia spanning the entire retina, where they ensheath all neuronal types from the RGC (bottom) to the photoreceptors. Modified from Histology of the Human Eye, an Atlas and Textbook. Hogan, Michael J., Jorge A. Alvarado, Joan Esperson Weddell. Philadelphia: W. B. Saunders, 1971.

FIGS. 2A-I depict rShH10 expression following intravitreal injection in the adult rat retina. Confocal imaging of immunostained transverse retinal sections 3 weeks post-injection of $2.5 \times 10^{10}$ viral particles (vector genomes) of dsCAG-GFP vectors with capsids from AAV2 (A-C), ShH10 (D-F), and AAV6 (G-I) (n=6). Glutamine synthetase (GS) staining (red) (B,E,H) and visualization of colocalization (C,F,I) reveals more robust Müller cell expression by ShH10 (E, F) relative to AAV2 (B,C), whereas AAV6 shows no visible expression (G-I). Additionally, GFP expression shows specific transduction of Müller cells by ShH10 (D) compared to AAV2 (A), which exhibits considerably more transduction of retinal ganglion cells and interneurons.

FIGS. 3A and 3B depict transduction specificity and efficiency of ShH10. Representative retinal slices from injected eyes were quantified for the number of each cell type that was infected, as determined via GFP expression, to generate histograms comparing tropism profiles (A) and Müller transduction efficiencies (B) of rAAV2, rShH10, and rAAV6 dsCAG-GFP. Transduction efficiencies were calculated based on the ratio of Müller cells infected relative to the total number of Müller cells in a 10 μm transverse retinal slice (n=6). Error bars represent standard deviation among sample population.

FIGS. 4A and 4B depict rShH10 expression in the whole retina following intravitreal injection. Fluorescence microscopy of transverse retinal sections from rShH10 CAG-GFP and rAAV6 CAG-GFP injected animals 3 weeks post-injection reveals broadly spread expression by ShH10 (B), with the most prominent expression localized at the injection site. AAV6 (A) shows no visible expression.

FIGS. 5A-D depict retinal astrocyte infectivity of ShH10. Fundus imaging of rShH10 CAG-GFP injected animals at one week (A) reveals a characteristic expression pattern localized near major vasculature and the optic nerve, which subsequently shows spreading after three weeks (B). Closer examination by flatmount (C) through laminin (red) and DAPI (blue) staining reveals a strong localization of GFP expression along the edges of retinal blood vessels, areas dense in retinal astrocytes. Transverse sections (D) stained for calbindin (red), a marker of RGCs and interneurons in the retina, illustrate a local region of expression within retinal astrocytes and Müller cells ensheathing a blood vessel.

Mutational Analysis of ShH10

Figure 6:
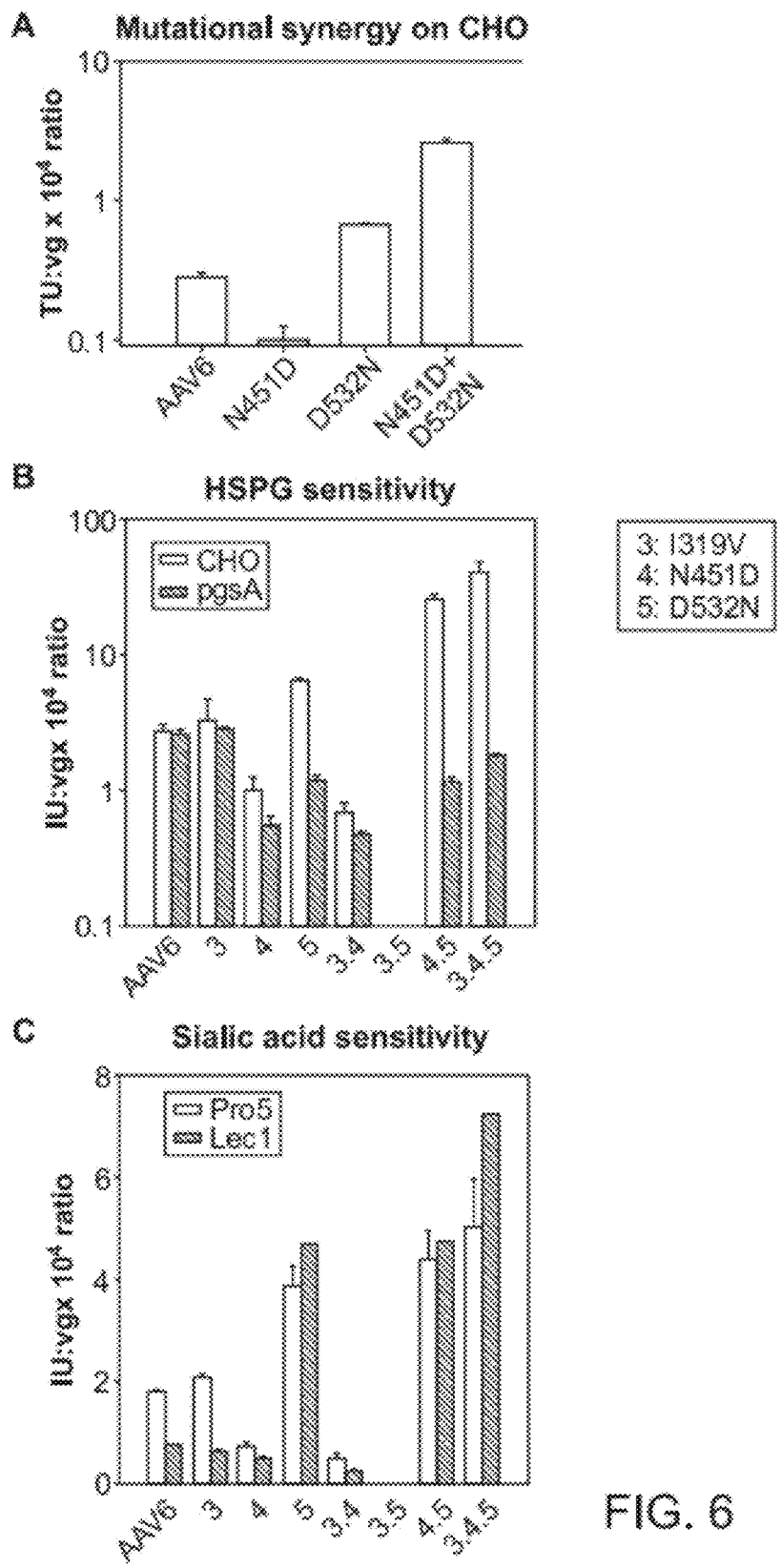
FIGS. 6A-C depict in vitro characterization of ShH10.

ShH10 is highly Müller cell selective, while AAV6 yields no detectable retinal expression upon intravitreal administration, yet ShH10 differs from AAV6 at only four residues: I319V, N451D, D532N, and H642N (FIG. 8)). To analyze the contributions of each of these mutations to ShH10's novel phenotype, single point mutants and all potential double mutants were generated from the AAV6 cap gene via site-directed mutagenesis. Each resulting variant was used to package rAAV-CMV-GFP and was purified via iodixanol gradient ultracentrifugation. To characterize the in vitro infectivity of these mutants, and in particular their glycan dependence in light of the substantial role proteoglycans and glycoproteins play in AAV transduction (Goncalves *Virol J.* 2005; 2:43; Xie et al. *Proc Natl Acad Sci USA.* 2002; 99:10405-10410; Wu et al. *J Virol.* 2006; 80:9093-9103), their relative transduction efficiencies were analyzed on a panel of cell types: Pro5, a Pro5 mutant (Lec1) deficient in N-linked sialic acid, CHO, and a CHO derivative (pgsA) deficient in all glycosaminoglycans. Bame et al. *J Biol Chem.* 1991; 266:10287-10293. AAV6 exhibited a dependence on N-linked sialic acids for efficient transduction, as previous studies have indicated (FIG. 6c). Wu et al. (2006) supra. However, the N451D mutation decreased the viral dependence on N-linked sialic acids, and the D532N mutation increased the viral transduction in the absence of N-linked sialic acids (FIG. 6c)). This D532N mutation, located near the HSPG binding domain of the AAV6 capsid (Wu et al. *J Virol.* 2006; 80:11393-11397), may enable the virus to utilize a transduction pathway distinct from AAV6 (FIG. 7).

Figure 9:
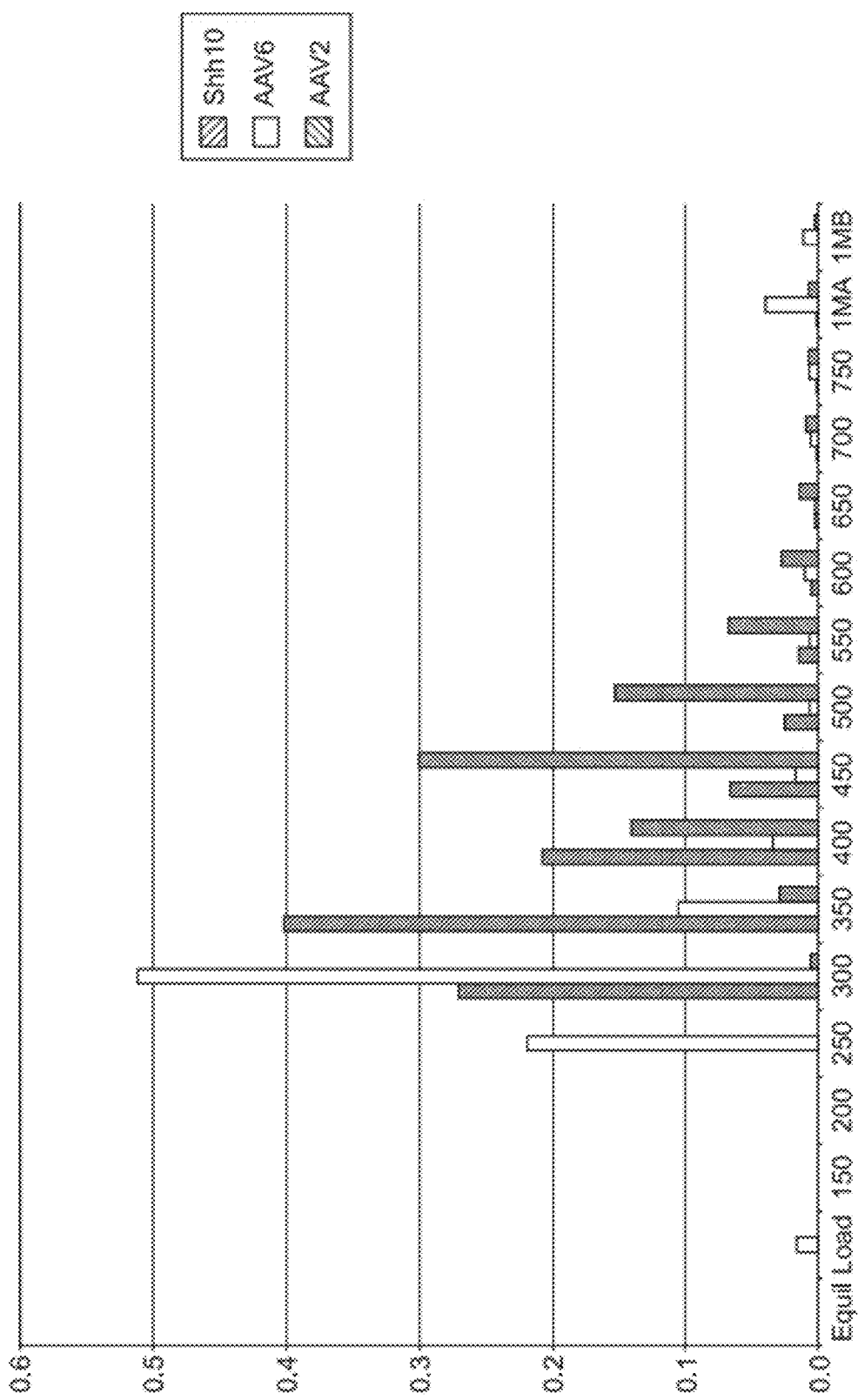
FIG. 9 depicts heparin binding affinity of ShH10, AAV2, and AAV6.
Figure 10:
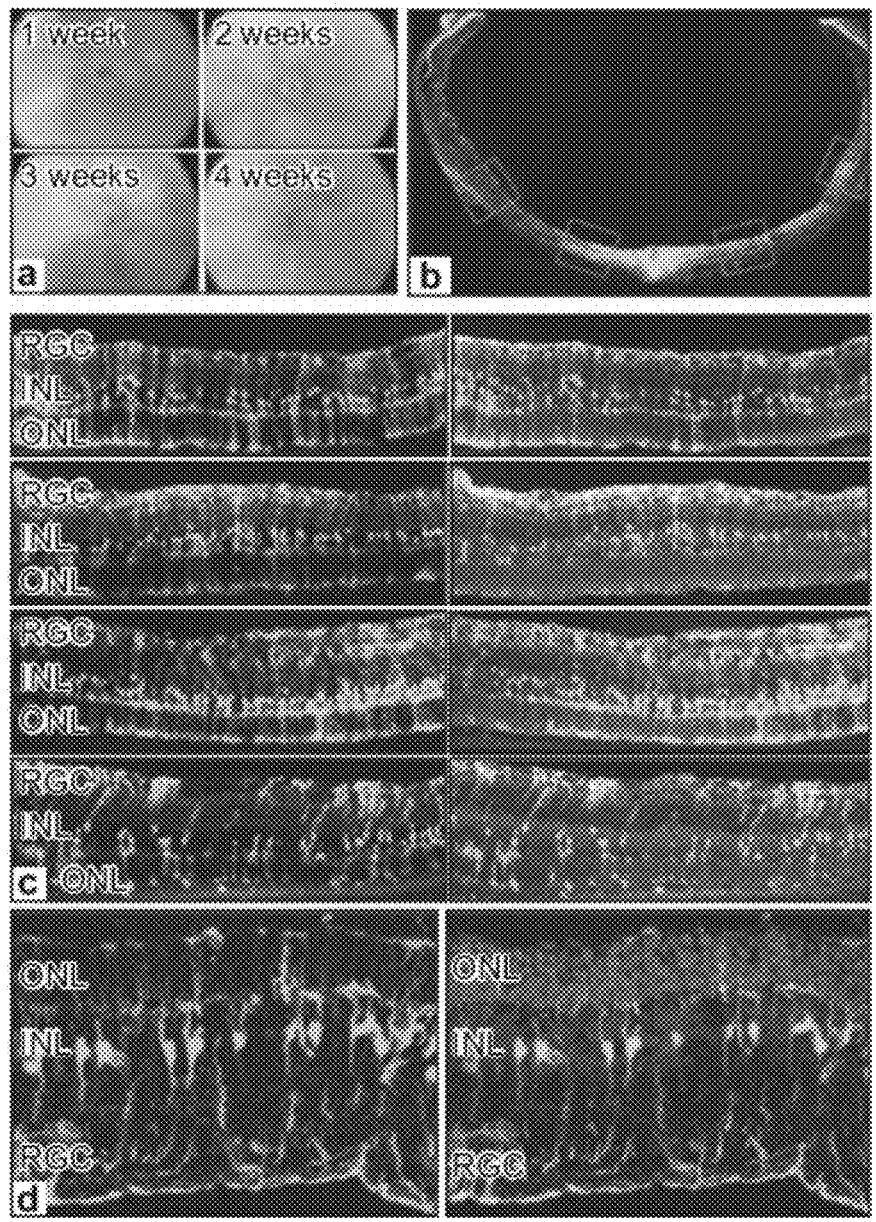
FIGS. 10A-D depict expression of ShH10.Y445F.scCAG-GFP in Müller cells after intravitreal injection.

Whereas AAV6 does not utilize HSPG for transduction (FIG. 6b) (Wu et al. *J Virol.* 2006; 80:9093-9103), several of the ShH10 mutations confer a new dependence on HSPG. Intriguingly, AAV6 N451D exhibited lower transduction levels relative to AAV6 in CHO cells, but when coupled with the D532N mutation was more infective than either AAV6 or AAV6 D532N (FIG. 6a). Comparing infection efficiencies among the single point mutants between CHO and pgsA cells, cell lines containing and lacking HSPG respectively, AAV6 D532N was the only mutant to exhibit a substantial HSPG dependence, which became more pronounced when coupled with mutations I319V and N451D (FIG. 6b). The enhanced infectivity of ShH10 is thus likely due to a synergy between mutations that in part augments HSPG affinity as suggested by the heparin affinity chromatogram (FIG. 9). To determine whether AAV6 mutations that enhance infectivity also function in vivo, equal titer intravitreal injections of $5 \times 10^9$ genomic particles of recombinant vector mutants carrying dsCAG-GFP revealed that that only AAV6 N451D was sufficient to confer the intravitreal Müller tropism. This mutant was considerably more efficient than AAV6 on Müller cells, though only half as efficient as ShH10 (FIGS. 3 and 7b).

FIGS. 6A-C depict in vitro characterization of ShH10. (A) CHO cell transduction by rAAV6, rAAV6 N451D, rAAV6 D532N, and rAAV6 N451D+D532N carrying CMV-GFP. (B) CHO/PgsA transduction demonstrating the HSPG dependence of various permutations of the mutations that comprise ShH10. (C) Pro5/Lec1 transduction examining sialic acid dependence of various permutations of the mutations that compose ShH10.

FIGS. 7A-C depict rAAV6 N451D expression following intravitreal injection. Confocal imaging of immunostained transverse retinal sections 3 weeks post-injection of rAAV6 N451D CAG-GFP (B, C). GFP expression analysis (B) and overlay with GS (C) reveal this mutant to be sufficient for an intravitreal Müller infection, though at a reduced efficiency relative to ShH10 (FIG. 1 D, F). Mapping of this mutation onto the AAV6 capsid subunit VP3 (A) (blue) shows its location near the three-fold axis of symmetry of the assembled capsid. Three-dimensional models of the AAV6 VP3 subunit were generated using Swiss Model with the coordinates of AAV2 (Protein Databank accession no. 1LP3) supplied as a template and images were rendered in Pymol and Rasmol. Additionally, the D532N mutation (green) maps near the HSPG-binding domain (purple).

FIGS. 8A-C depict amino acid sequences of wild-type and variant AAV capsids.

FIG. 9 depicts the elution profile from a heparin column for ShH10, AAV2, and AAV6. The Y-axis values represent the fraction of virus eluted, and the X-axis represents the concentration of NaCl in the eluant (mM).

Example 2

AAV-Mediated GDNF Secretion from Retinal Glia Slows Retinal Degeneration

Materials and Methods:
Generation of rAAV Vectors:
AAV vectors were produced by the plasmid co-transfection method. Grieger et al. (2006) *Nat Protoc* 1: 1412-1428, rAAV was purified via iodixanol gradient ultracentrifugation (Dalkara, D, et al. (2009) *Mol Ther* 17: 2096-2102) and heparin column chromatography (GE Healthcare, Chalfont St. Giles, UK). The viral eluent was desalted and concentrated with Amicon Ultra-115 Centrifugal Filter Units to a final volume of 200 μl and titered by quantitative polymerase chain reaction (qPCR) relative to standards.

Intraocular Injections:
TgS334-4ter rats were used for all studies, and all animal procedures were conducted according to the ARVO Statement for the Use of Animals and the guidelines of the Office of Laboratory Animal Care at the University of California, Berkeley. Rats were first anesthetized with ketamine (72 mg/kg) and xylazine (64 mg/kg) by intraperitoneal injection. An ultrafine 30½-gauge disposable needle was then passed through the sclera, at the equator and next to the limbus, into the vitreous cavity. Five μl, containing $1-5\times10^{12}$ vg/ml of AAV were injected with direct observation of the needle in the center of the vitreous cavity.

Cryosections:
Animals were humanely euthanized by $CO_2$ overdose and cervical dislocation. Eyes were enucleated and immersion fixed in 10% formalin. The cornea and lens were removed and the resulting eye-cups were cryoprotected in 30% sucrose before embedding in OCT compound (Miles Diagnostics, Elkhart, Ind.). 5-10 μm thick transverse retinal sections were cut.

Immunolabeling:
Tissue sections were blocked in 1% BSA, 0.5% Triton X-100, and 2% normal donkey serum for 2-3 hours and treated with a rabbit anti-glutamine synthetase monoclonal antibody (Sigma G2781) at a 1:3000 dilution in blocking solution overnight at 4° C. After 3 PBS washes, Cy3-conjugated anti-rabbit secondary (GE Healthcare) was applied at a 1:1000 dilution in blocking solution for 2 hours at room temperature. The results were examined by confocal microscopy (LSM5; Carl Zeiss Microimaging).

Electroretinography:
Rats were dark-adapted for minimum of 2 hours and then anesthetized, followed by pupil dilation. Contact lenses were positioned on the cornea of both eyes. Reference electrodes were inserted subcutaneously in the cheeks and a ground electrode was inserted in the tail. Electroretinograms were recorded (Espion ERG system; Diagnosys LLC, Littleton, Mass.) in response to seven light flash intensities ranging from −4 to 1 log $cd*s/m^2$. Each stimulus was presented in series of three. Light flash intensity and timing were computer controlled. Data were analyzed with MatLab (v7.7; Mathworks, Natick, Mass.). ERG a and b waves from control and treated eyes were compared using Mann-Whitney paired t test.

Histology:
Rats were euthanized by $CO_2$ overdose. The superior cornea was marked, and enucleated eyes were immersion fixed in formalin followed by removal of cornea and lens. Eye cups were then fixed in 1% osmium tetroxide, dehydrated by incubation in increasing ethanol concentrations and a final incubation in 100% propylene oxide. The samples were then embedded in an epon-araldite resin and hardened overnight at 65° C. One μm thin plastic sections were cut along the vertical meridian, through the optic nerve with a sapphire blade. Measurements of ONL, IPL and OS thickness from the optic nerve head (ONH) to ora serrata in 3 rats 3 months post treatment were made on high resolution montages of the retinas imaged at 40× using ImageJ software. Fifty four measurements of the ONL, IPL and OS were made at 18 contiguous fields around the entire retinal section (3 measurements per field). These measurements were plotted as a distribution of thickness across the central retina.

ELISA:
Brief sonication was used to homogenize treated and control retinas. ELISA was performed using the DuoSet Kit for human GDNF (R&D systems) according to the manufacturer's instructions.

Results

ShH10 Leads to Selective and Efficient Targeting of Müller Glia in a Rat Model of RP.

As described in Example 1, the engineered AAV variant ShH10 had revealed efficient and specific transduction of rat Müller glia in wild-type animals. Klimczak, et al. (2009) *PLoS One* 4: e7467. Since high-level GDNF expression is of interest, the infectivity of ShH10 was further enhanced by mutating a surface exposed tyrosine residue to phenylalanine for potentially more efficient trafficking to the nucleus. Petrs-Silva, H, et al. (2009) *Mol Ther* 17: 463-471; and Zhong, L, et al. (2008) *Proc Natl Acad Sci USA* 105: 7827-7832. Intravitreal injection of this recombinant ShH10.Y445F variant with a scCAG.GFP transgene in S334-4ter rats revealed strong, selective expression in Müller cells throughout the retina, peaking 3 weeks post injection (FIG. 10a-e). Furthermore, 53% of all Müller cells showed GFP expression in TgS334-ter retinas infected with ShH10.Y445F. This indicates a significant increase compared to the number of Müller cells infected in wild type retinas after ShH10 vector introduction. Klimczak, et al. (2009) *PLoS One* 4: e7467. This is likely due to an increased transduction efficiency afforded by the additional tyrosine mutation, alongside the more permissive nature of degenerating retinas to AAV mediated transduction. Kolstad, et al. (2010) *Hum Gene Ther* 21: 571-578.

FIGS. 10A-E. ShH10.Y445F.scCAG-GFP drives strong pan-retinal expression in Müller cells when intravitreally injected into S334-4ter rat eyes. (a) Representative fundus images at 1 to 4 weeks post injection into p15 S334-ter rat eyes show rapid onset of expression at 1 week post injection before peaking and stabilizing at 3-4 weeks. (b) High resolution montage of a retinal cryosection through the ONH showing the extent of GFP expression in Müller cells throughout the retina. (c) Low magnification (10×) images at 4 representative regions of the retinal cryosection. Left hand panels show GFP expression in Müller cells while right hand panels also show glutamine synthase staining (in red) and nuclei stained with DAPI in blue. (d) High magnification image (40×) showing selective GFP expression in Müller cells in green alongside an overlay of GFP with glutamine synthase-staining (red) and DAPI-staining (blue).

Figure 11:
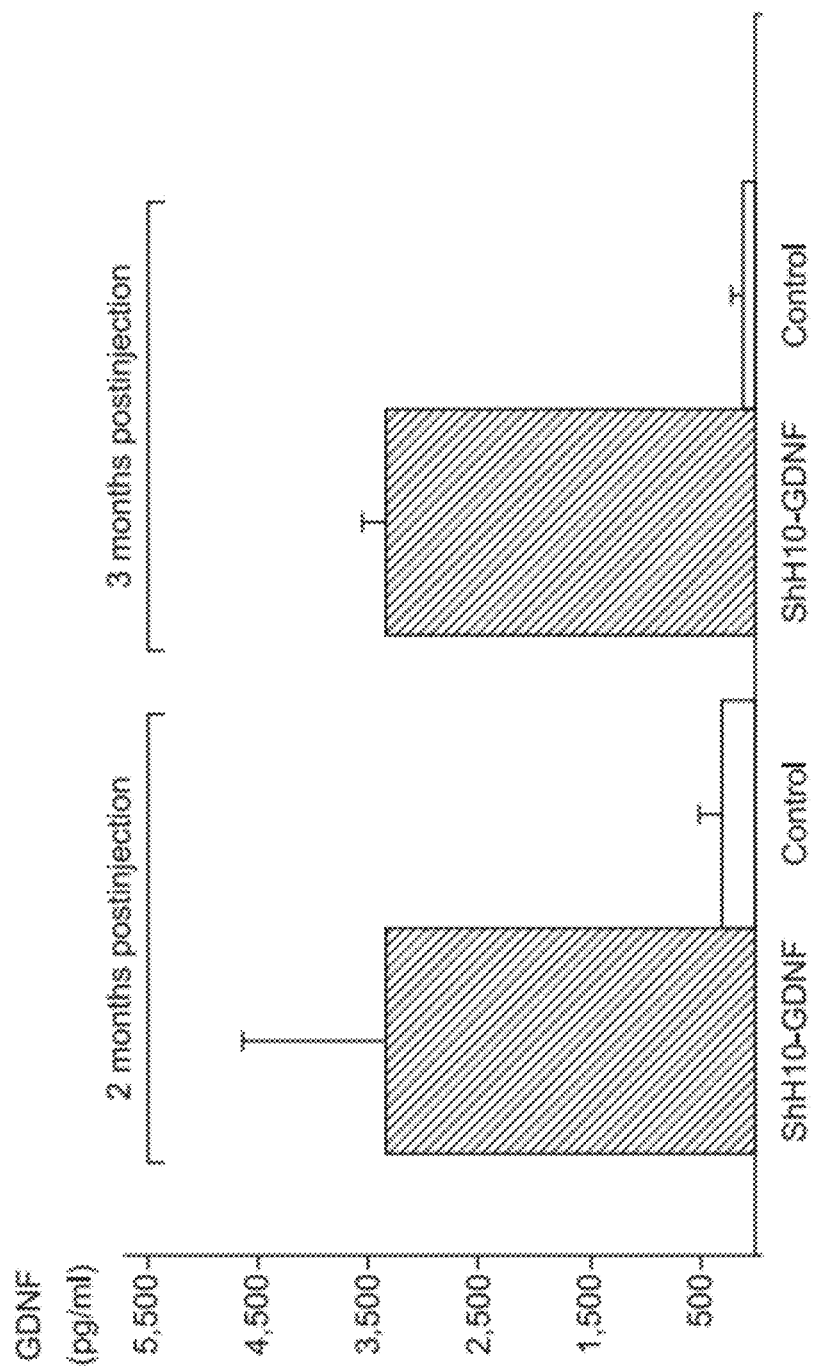
FIG. 11 depicts enzyme-linked immunosorbent assay (ELISA) measurements of human glial-derived neurotrophic factor (hGDNF) protein in retinal homogenates 2 and 3 months following intravitreal delivery of ShH10.Y445F.scCAG-hGDNF.

Given the high specificity of the vector, a self-complementary hGDNF transgene driven from the same promoter, was inserted. Yokoi, K, et al. (2007) *Invest Ophthalmol Vis Sci* 48: 3324-3328; and McCarty, D M (2008) *Mol Ther* 16: 1648-1656. Following intravitreal delivery of ShH10.Y444F scCAG.hGDNF, enzyme-linked immunosorbent assay (ELISA) measurements revealed robust secretion of hGDNF from Müller cells both two and three months post injection (FIG. 11). At more than 2.5 ng/mL, these hGDNF levels are nearly 10-fold higher than those produced in previous studies that have achieved photoreceptor degeneration rescue through GDNF overexpression from retinal neurons after subretinal injection (Frasson, M, et al. (1999) *Invest Ophthalmol Vis Sci* 40: 2724-2734; McGee et al. (2001) *Mol Ther* 4: 622-629) or from intraocularly-placed mouse embryonic stem cells (Gregory-Evans, et al. (2009) *Mol Vis* 15: 962-973). Importantly, the expression is sustained, as ELISA measurements of GDNF in the vitreous of rats 5 months post injection show elevated levels of the therapeutic protein, which are both safe (Wu, et al. (2005) *Curr Eye Res* 30: 715-722) and necessary for sustained rescue.

FIG. 11. ELISA measurements of hGDNF protein in retinal homogenates two (n=7) and three months (n=6) following intravitreal delivery of ShH10.Y444F.scCAG.hGDNF. All animals received hGDNF vector treatment in the right eye and no injection in the left eye.

Müller Cell Secretion of GDNF Slows Down Retinal Degeneration in S334-4ter Rats

Figure 12:
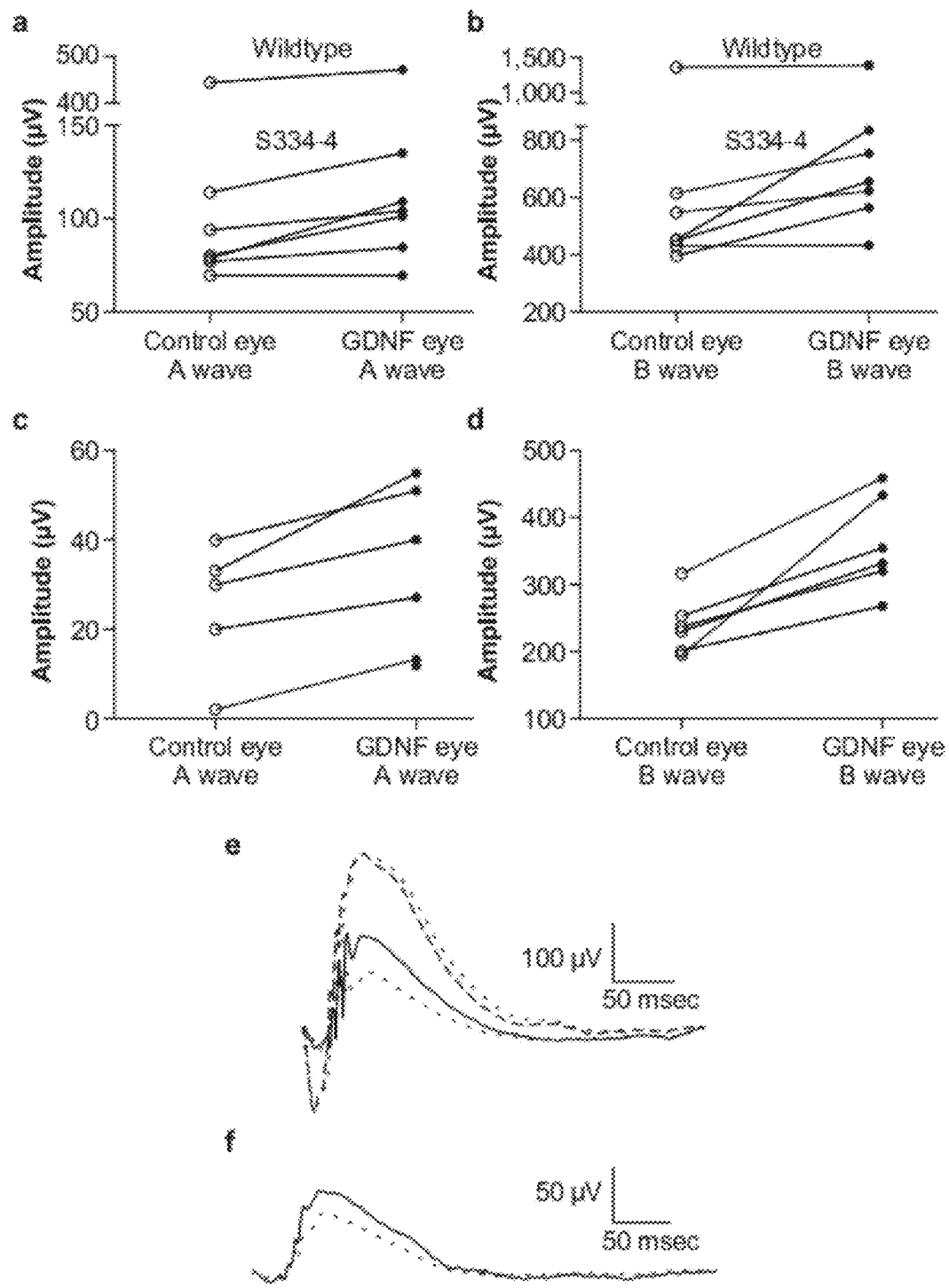
FIGS. 12A-F depict scatter plots of electroretinography (ERG) measurements following GDNF delivery to the eye using a rAAV of the present disclosure.

Electroretinography (ERG) was used to assess the visual function of S334-4ter animals injected intravitreally at P15 with ShH10.Y445F.scCAG-GDNF. At one month post-injection, small increases were seen in both a and b-wave amplitudes of the treated eyes relative to untreated eyes (either uninjected or injected with ShH10.Y444F.scCAG-GFP) (FIG. 12a-b, e). Although the ERG amplitudes were heterogeneous among animals, rescue was consistent between the control and contralateral GDNF-injected eyes, with an average b-wave value of 644 µV (+/−142 µV) in treated eyes versus 481 µV (+/−82 µV) for the control eyes (FIG. S3a). Wild-type animals demonstrated a-wave amplitudes of approximately 455 µV (FIG. 12a) and b-wave amplitudes of 1370 µV at the same age (FIG. 12b). Remarkably, from 3 to 5 months after the injection, the physiological rescue became more pronounced, with an average amelioration of 50% in b-wave amplitude amongst all animals at 5 months and a nearly two-fold increase observed in one animal (FIG. 12d), with similar improvements in a-wave amplitudes (FIG. 12c). Representative ERG traces corresponding to the average values at one (FIG. 12e) and five (FIG. 12f) months post injection are shown below.

FIGS. 12A-F. Scatter plots of ERG a (a) and b-wave (b) amplitudes in response to 1 log cd*s/m2 in GDNF-treated and contralateral control eyes 1 month post-injection and at 5 months (c, d). All animals (n=6) were injected at p15. Representative ERG traces at 1 log cd*s/m2 from a wild type animals eyes (gray solid and dotted traces) and an animal with GDNF-treated (solid black line) versus control eye (dotted black line) at 1 month post-injection (e). Representative ERG trace at 1 log cd*s/m2 from a GDNF-treated animal (solid black line) versus contralateral control eye (dotted black line) at 5 months (f).

Histological Rescue of Photoreceptors

Figure 13:
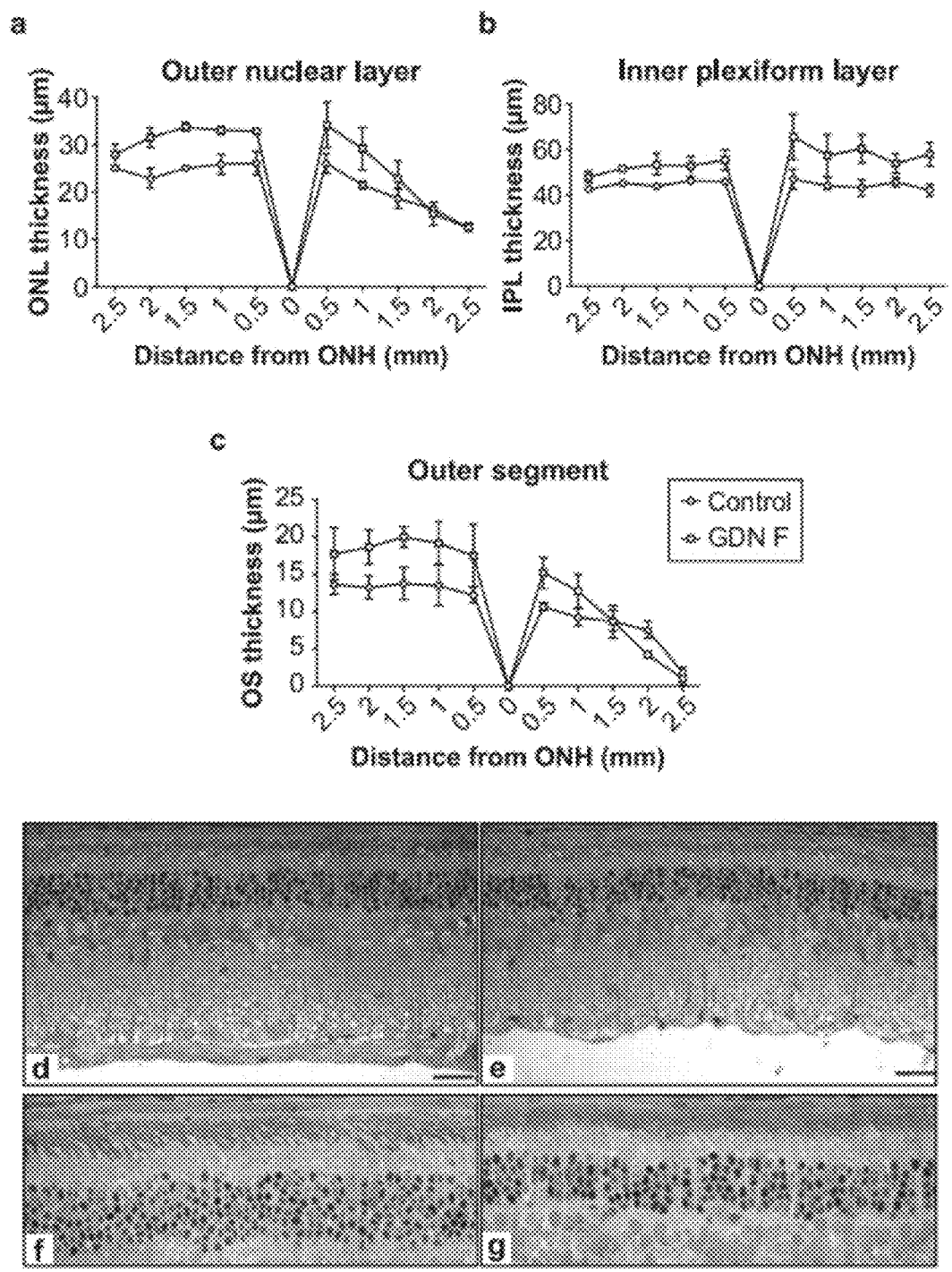
FIGS. 13A-G depict measurements of outer nuclear layer thickness, inner plexiform layer thickness, and photoreceptor outer segment length along the vertical meridian of the eye from the optic nerve head to the ora senate in rats at 3 months postinjection.

Histological rescue was determined by measuring the thickness of the outer nuclear layer (ONL), a well-established indicator of photoreceptor survival. Histological examination of GDNF-injected and control retinas corroborate the preservation of function observed in the electroretinograms. The ONLs of superior and inferior GDNF-treated retinas were thicker up to 4 mm from the optic nerve head at the inferior retina and up to 2 mm from the optic nerve at the superior retinas at 3 months post-injection (FIG. 13a). Additionally, the inner plexiform layer and the photoreceptor outer segments were shorter in most of the inferior and a fraction of the superior control retinas (FIG. 13a-c).

FIGS. 13A-G. Measurements of outer nuclear layer thickness (a) inner plexiform layer thickness (b) and photoreceptor outer segment length (c) along the vertical meridian of the eye from the optic nerve head (ONH) to the ora serrata in rats at 3 months post injection (p105). Rats were either uninjected (full circles) or injected with ShH10.Y445F.scCAG.GDNF (squares) at p15. Light micrographs from inferior retinas of ShH10.Y445F.scCAG.GDNF injected (d) of uninjected (e) rats at 20× magnification, scale bars are 25 µm. High magnification micrographs from inferior retinas of ShH10.Y445F.scCAG.GDNF injected (e) or uninjected (f) rats at 40× magnification, showing differences in outer segments length in the central part of inferior retinas.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant adeno-associated virus (rAAV) virion comprising:
   a) a variant AAV capsid protein, wherein the variant AAV capsid protein comprises an amino acid substitution at amino acid 451 of the AAV6 capsid sequence as set forth in SEQ ID NO:1, or the corresponding position in another AAV parental serotype, and wherein the variant capsid protein confers increased infectivity of a retinal cell compared to the infectivity of the retinal cell by an AAV virion comprising a wild-type AAV capsid protein, wherein the AAV capsid protein does not comprise an amino acid sequence present in a naturally occurring AAV capsid protein; and
   b) a heterologous nucleic acid comprising a nucleotide sequence encoding a gene product.

2. The rAAV virion of claim 1, wherein the retinal cell is a Müller glial cell.

3. The rAAV virion of claim 1, wherein the rAAV virion exhibits at least 5-fold increased infectivity of a retinal cell compared to the infectivity of the retinal cell by an AAV virion comprising the corresponding parental AAV capsid protein.

4. The rAAV virion of claim 1, wherein the rAAV virion exhibits at least 50-fold increased infectivity of a retinal cell compared to the infectivity of the retinal cell by an AAV virion comprising the corresponding parental AAV capsid protein.

5. The rAAV virion of claim 1, wherein gene product is a nucleic acid gene product.

6. The rAAV virion of claim 5, wherein the nucleic acid gene product is an interfering RNA, a ribozyme, an antisense nucleic acid, or an aptamer.

7. The rAAV virion of claim 1, wherein the gene product is a polypeptide.

8. The rAAV virion of claim 7, wherein the polypeptide is a neuroprotective polypeptide.

9. The rAAV virion of claim 7, wherein the polypeptide is glial derived neurotrophic factor, fibroblast growth factor 2, nurturin, ciliary neurotrophic factor, nerve growth factor, brain derived neurotrophic factor, epidermal growth factor, a soluble vascular endothelial growth factor (VEGF) receptor, an anti-VEGF antibody, or Sonic hedgehog.

10. The rAAV virion of claim 7, wherein the polypeptide is an anti-angiogenic polypeptide.

11. The rAAV virion of claim 1, wherein the parental AAV capsid protein is wild-type AAV6 capsid protein.

12. The rAAV virion of claim 6, wherein the interfering RNA or the aptamer reduces the level of an angiogenic factor in the retinal cell.

13. The rAAV virion of claim 1, wherein the variant capsid protein provides for selective infection of a Müller glial cell compared to other cells in the eye.

14. The rAAV virion of claim 1, wherein the variant AAV capsid protein comprises an amino acid change at AAV6 position 532 or the corresponding position in another AAV parental serotype.

15. The rAAV virion of claim 14, wherein the amino acid substitution at amino acid 532 of AAV6, or the corresponding position in another AAV parental serotype, is an asparagine.

16. The rAAV virion of claim 1, wherein the amino acid substitution at amino acid 451 of AAV6, or the corresponding position in another AAV parental serotype, is an aspartic acid protein comprises.

17. The rAAV virion of claim 1, wherein the variant AAV capsid protein comprises an asparagine to aspartic acid substitution at amino acid 451 of AAV6, or the corresponding position in another AAV parental serotype and an aspartic acid to asparagine substitution at amino acid 532 of AAV6, or the corresponding position in another AAV parental serotype.

18. The rAAV virion of claim 1, wherein the variant capsid protein comprises from 1 to 10 amino acid differences compared to a wild-type AAV capsid protein.

19. The rAAV virion of claim 1, wherein the retinal cell is a retinal glial cell.

20. The rAAV virion of claim 1, wherein the retinal cell is an astrocyte.

21. A pharmaceutical composition comprising:
   a) a recombinant adeno-associated virus (rAAV) virion according to claim 1; and
   b) a pharmaceutically acceptable carrier, diluent, excipient, or buffer.

22. A method of delivering a gene product to a retinal cell in an individual, the method comprising administering to the individual a recombinant adeno-associated virus (rAAV) virion according to claim 1.

23. The method of claim 22, wherein the gene product is a polypeptide.

24. The method of claim 22, wherein the gene product is a nucleic acid.

25. The method of claim 23, wherein the polypeptide is a neuroprotective factor or an anti-angiogenic factor.

26. The method of claim 25, wherein the polypeptide is glial derived neurotrophic factor, fibroblast growth factor 2, nurturin, ciliary neurotrophic factor, nerve growth factor, brain derived neurotrophic factor, epidermal growth factor, a soluble vascular endothelial growth factor (VEGF) receptor, an anti-VEGF antibody, or Sonic hedgehog.

27. A method of treating a retinal disease, the method comprising administering to an individual in need thereof an effective amount of a recombinant adeno-associated virus (rAAV) virion according to claim 1.

28. The method of claim 27, wherein said administering is by intraocular injection.

29. The method of claim 27, wherein said administering is by intravitreal injection.

30. The method of claim 27, wherein the ocular disease is glaucoma, retinitis pigmentosa, or macular degeneration.

31. An isolated nucleic acid comprising a nucleotide sequence that encodes a variant adeno-associated virus (AAV) capsid protein, wherein the variant AAV capsid protein comprises an amino acid substitution at amino acid 451 of the AAV6 capsid sequence as set forth in SEQ ID NO:1, or the corresponding position in another AAV parental serotype, and wherein the variant capsid protein, when present in an AAV virion, provides for increased infectivity of the AAV virion for a retinal cell.

32. An isolated, genetically modified host cell comprising the nucleic acid of claim 31.

33. A variant AAV capsid protein, wherein the variant AAV capsid protein comprises an amino acid change at AAV6 position 532 or the corresponding position in another AAV parental serotype and wherein the variant capsid protein confers increased infectivity of a Müller glial cell compared to the infectivity of the Müller glial cell by an AAV virion comprising a wild-type AAV capsid protein, wherein the AAV capsid protein does not comprise an amino acid sequence present in a naturally occurring AAV capsid protein.

34. The capsid protein of claim 33, where the amino acid change is D532N, alone or in combination with N451D.

35. A nucleic acid encoding a variant AAV capsid, wherein the nucleic acid encodes an amino acid change at AAV6 position 532 or the corresponding position in another AAV parental serotype and wherein the variant capsid protein confers increased transduction of a Müller glial cell compared to the transduction of the Müller glial cell by an AAV virion comprising a wild-type AAV capsid protein, wherein the AAV capsid protein does not comprise an amino acid sequence present in a naturally occurring AAV capsid protein.

36. The nucleic acid of claim 35, where the amino acid change is D532N, alone or in combination with N451D.

* * * * *

UNITED STATES PATENT AND TRADEMARK OFFICE
CERTIFICATE OF CORRECTION

| | | |
|---|---|---|
| PATENT NO. | : 8,663,624 B2 | Page 1 of 1 |
| APPLICATION NO. | : 13/253760 | |
| DATED | : March 4, 2014 | |
| INVENTOR(S) | : David V. Schaffer | |

It is certified that error appears in the above-identified patent and that said Letters Patent is hereby corrected as shown below:

In the claims

Col. 66, Lines 20-23, claim 16 should read:

--The rAAV virion of claim 1, wherein the amino acid substitution at amino acid 451 of AAV6, or the corresponding position in another AAV parental serotype, is an aspartic acid.--

Signed and Sealed this
Second Day of September, 2014

Michelle K. Lee
*Deputy Director of the United States Patent and Trademark Office*